US008841083B2

(12) United States Patent
Heath et al.

(10) Patent No.: US 8,841,083 B2
(45) Date of Patent: Sep. 23, 2014

(54) PSA CAPTURE AGENTS, COMPOSITIONS, METHODS AND PREPARATION THEREOF

(75) Inventors: James R. Heath, South Pasadena, CA (US); Heather Dawn Agnew, Culver City, CA (US); Suresh Mark Pitram, La Jolla, CA (US)

(73) Assignees: California Institute of Technology, Pasadena, CA (US); Indi Molecular, Inc., Culver City, CA (US)

( * ) Notice: Subject to any disclaimer, the term of this patent is extended or adjusted under 35 U.S.C. 154(b) by 0 days.

(21) Appl. No.: 13/366,196

(22) Filed: Feb. 3, 2012

(65) Prior Publication Data

US 2012/0202219 A1 Aug. 9, 2012

Related U.S. Application Data

(60) Provisional application No. 61/439,362, filed on Feb. 3, 2011.

(51) Int. Cl.
| | |
|---|---|
| C07K 14/00 | (2006.01) |
| C07K 1/107 | (2006.01) |
| C07K 7/08 | (2006.01) |
| G01N 33/573 | (2006.01) |

(52) U.S. Cl.
USPC ......................................................... 435/7.4

(58) Field of Classification Search
None
See application file for complete search history.

(56) References Cited

U.S. PATENT DOCUMENTS

| 7,521,541 B2 * | 4/2009 | Eigenbrot et al. ......... 530/387.1 |
| 2005/0025709 A1* | 2/2005 | McBride et al. ............. 424/9.34 |
| 2008/0312141 A1 | 12/2008 | Stenman et al. |

OTHER PUBLICATIONS

Agnew (PhD dissertation entitled "Rapid Construction of Protein Capture Agents with Chemically Designed Stability and Antibody-Like Recognition Properties", http://thesis.library.caltech.edu/5583/11/Thesis.pdf).*
Agnew et al. (Angew Chem Int Ed Engl., 48(27):4944-4948, 2009).*
Acevedo, B., et al., "Development and Validation of a Quantitative ELISA for the Measurement of PSA Concentration," Clinica Chimica Acta 317:55-63 (2002).
Agnew, H. D., et al., "Iterative In Situ Click Chemistry Creates Antibody-Like Protein-Capture Agents," Angew. Chem. Int. Ed. 48:4944-4948 (2009).
Boren, B. C., et al., "Ruthenium-Catalyzed Azide-Alkyne Cycloaddition: Scope and Mechanism," J. Am. Chem. Soc. 130:8923-8930 (2008).
Fields, G. B., et al., "Solid Phase Peptide Synthesis Utilizing 9-Fluorenylmethoxycarbonyl Amino Acids," Int. J. Peptide Protein Res. 35:161-214 (1990).
Jeong, S., et al., "Expression and Purification of Recombinant Active Prostate-Specific Antigen from *Escherichia coli*," J. Microbiol. Biotechnol. 17(5):840-846 (2007).
Lee, S., et al., "Rapid Microwave-Assisted CNBr Cleavage of Bead-Bound Peptides," J. Comb. Chem. 10(6):807-809 (2008).
Lee, S., et al., "Accurate MALDI-TOF/TOF Sequencing of One-Bead-One-Compound Peptide Libraries with Application to the Indentification of Multi-Ligand Protein Affinity Agents Using In Situ Click Chemistry Screening," Anal. Chem. 82(2):672-679 (2010).
Pakkala, M., et al., "Activity and Stability of Human Kallikrein-2-Specific Linear and Cyclic Peptide Inhibitors," J. Pept. Sci. 13: 348-353 (2007).
Wu, P., et al., "Identification of Novel Prostate-Specific Anitgen-Binding Peptides Modulating Its Enzyme Activity," Eur. J. Biochem. 267:6212-6220 (2000).
Agnew, Rapid Construction of Protein Capture Agents With Chemically Designed Stability and Antibody-Like Recognition Properties. http://thesis.library.caltech.edu/5583/11lfthesis.pdf. (2010) Retrieved May 2, 2012 p. 38. Fig. 2.4, p. 65-68, p. 89, p. 111, Fig. 4.5, p. 112-113.
Chen et al. microPET and Autoradiographic Imaging of GRP Receptor Expression with 64Cu-DOTA-[Lys3]Bombesin in Human Prostate Adenocarcinoma Xenografts. J Nucl Med 2004; 45:1390-1397 Abstract.
Huhtinen et al. Immunoassay of total prostate-specificantigen using europium(III) nanoparticle labels and streptavidin-biotin technology. Journal of Immunological Methods vol. 294, Nov. 2004, Abstract, pp. 111-122.
Kodadek, Development of protein-detecting microarrays and related devices. Trends in Biochemical Sciences vol. 27. No. 6 Jun. 2002 p. 297, col. 2.
International Search Report & Written Opinion from PCT/US 12/23873, dated Jul. 2, 2012.

* cited by examiner

*Primary Examiner* — Alana Harris Dent
*Assistant Examiner* — Nelson B Moseley, II
(74) *Attorney, Agent, or Firm* — Lathrop & Gage LLP

(57) ABSTRACT

Disclosed herein are novel synthetic prostate specific antigen (PSA)-targeted capture agents that specifically bind PSA. In certain embodiments, these PSA capture agents are biligand or triligand capture agents containing two or three target-binding moieties, respectively.

23 Claims, 24 Drawing Sheets

(a)

PSA anchor ligand (I)

(b)

PSA Tz5-biligand (I)

(c)

PSA Tz5-triligand (I)

(d)

PSA Tz4-biligand (I)

(e)

PSA Tz4-triligand (I)

Side-Chain Protected PSA Tz5-Biligand (I)

Side-Chain-protected PSA Tz5-Triligand

| | %CV (interassay) | | |
|---|---|---|---|
| PSA (ng/mL) | Tz5Tz5-rrivk triligand | PS1 mAb | Tz5-biligand |
| 2627 | 13.6 | 8.0 | 14.3 |
| 291 | 5.8 | 15.2 | 14.7 |
| 32.4 | 17.8 | 14.9 | 14.3 |
| 10.8 | 13.9 | 20.3 | 32.5 |
| 8 | 12.4 | 22.2 | 31.1 |
| 5.12 | 23.6 | 25.0 | 30.3 |
| 3.28 | 30.5 | 20.8 | 32.7 |
| 1.2 | 46.5 | 11.4 | 40.7 |

(a)

(b)

(c)

PSA CAPTURE AGENTS, COMPOSITIONS, METHODS AND PREPARATION THEREOF

RELATED APPLICATIONS

The present application claims priority to U.S. Provisional Patent Application No. 61/439,362, filed Feb. 3, 2011, the disclosure of which is incorporated by reference herein in its entirety.

STATEMENT REGARDING FEDERALLY SPONSORED RESEARCH OR DEVELOPMENT

This invention was made with government support under Grant No. 5U54CA151819-03 awarded by the National Cancer Institute. The government has certain rights in the invention.

BACKGROUND

Prostate cancer is a commonly diagnosed cancer in men and a leading cause of cancer death. If detected at an early and treatable stage, prostate cancer is curable. Unfortunately, a majority of cases are diagnosed at later stages when metastasis of the primary tumor has already occurred. Even early diagnosis is controversial because not all individuals who test positive in prostate cancer screens develop cancer.

Prostate specific antigen (PSA) is a serum glycoprotein member of the glandular kallikrein gene family. PSA has a restricted chymotrypsin-like enzyme activity cleaving C-terminally to tyrosine and leucine residues on semenogelin I, the natural substrate of PSA. The tissue specificity of PSA makes it useful as both a diagnostic target and as a potential therapeutic target for active specific immunotherapy. Prostate specific antigen can be detected at low levels in the sera of healthy males without clinical evidence of prostate cancer. During neoplastic states, however, circulating levels of PSA increase dramatically. These increases frequently correlate with the clinical stage of the disease. Therefore, PSA is widely used as a marker for both screening and stratification of prostate cancer, with levels greater than 4 ng/mL considered to be a reliable indicator of prostate cancer (Jeong 2007). In serum, two different forms of PSA are immunologically detectable: a free form (MW=30 kDa) and a complex with α-1-antichymotrypsin (ACT-PSA, MW=100 kDa). Equimolar total PSA determination (free PSA+ACT-PSA), the ratio between total PSA and free PSA, digital rectal examination (DRE), and biopsy are included in multiple prostate cancer diagnostic algorithms. The ratio between total PSA and free PSA also may provide distinguishing information between cancer and benign prostatic hyperplasia (BPH), which is a common misdiagnosis. Measuring total PSA for diagnostic or follow-up purposes requires assays that detect a broad range (0.1 to 20 ng/mL) of concentrations (Acevedo 2002).

Current PSA screening tests utilize a monoclonal antibody (mAb) as a capture agent to detect PSA in a blood sample. These tests have several limitations inherent to monoclonal antibody technology. First, monoclonal antibody instability results significant costs and limitations in shipping, handling, and storage. Second, monoclonal antibodies are not exact chemical structures, meaning they can exhibit significant batch-to-batch variation in composition. This can lead to variations in capture affinity and selectivity between batches, leading to issues with the quantitative character of protein assays. Consequently, there is a need in the art for improved PSA capture agents to replace monoclonal antibodies for use in both screening for and treating prostate cancer.

SUMMARY

Provided herein in certain embodiments are synthetic PSA capture agents that specifically bind PSA. In certain embodiments, these capture agents comprise one or more target-binding moieties, and in certain of these embodiments the target-binding moieties are peptides. In certain embodiments, the capture agents are biligand or triligand capture agents, meaning that they comprise two or three target-binding moieties, respectively. In certain of these embodiments, the capture agents are cyclic biligands or triligands. In certain embodiments, the target-binding moieties within a capture agent are linked together via a covalent linkage such as an amide bond or a 1,4- or 1,5-disubstituted-1,2,3-triazole linkage, and in certain embodiments the target-binding moieties are linked together via Tz5 or Tz4 linkage. In certain embodiments, the capture agents provided herein are stable across a wide range of temperatures, pH's, storage times, storage conditions, and reaction conditions, and in certain embodiments the capture agents are more stable across one or more of these conditions than a comparable antibody.

In certain embodiments, a PSA capture agent provided herein is a Tz5-triligand comprising an anchor ligand, secondary ligand, and tertiary ligand comprising the amino acid sequence set forth in SEQ ID NOs:1, 2, and 3, respectively, and having the structure:

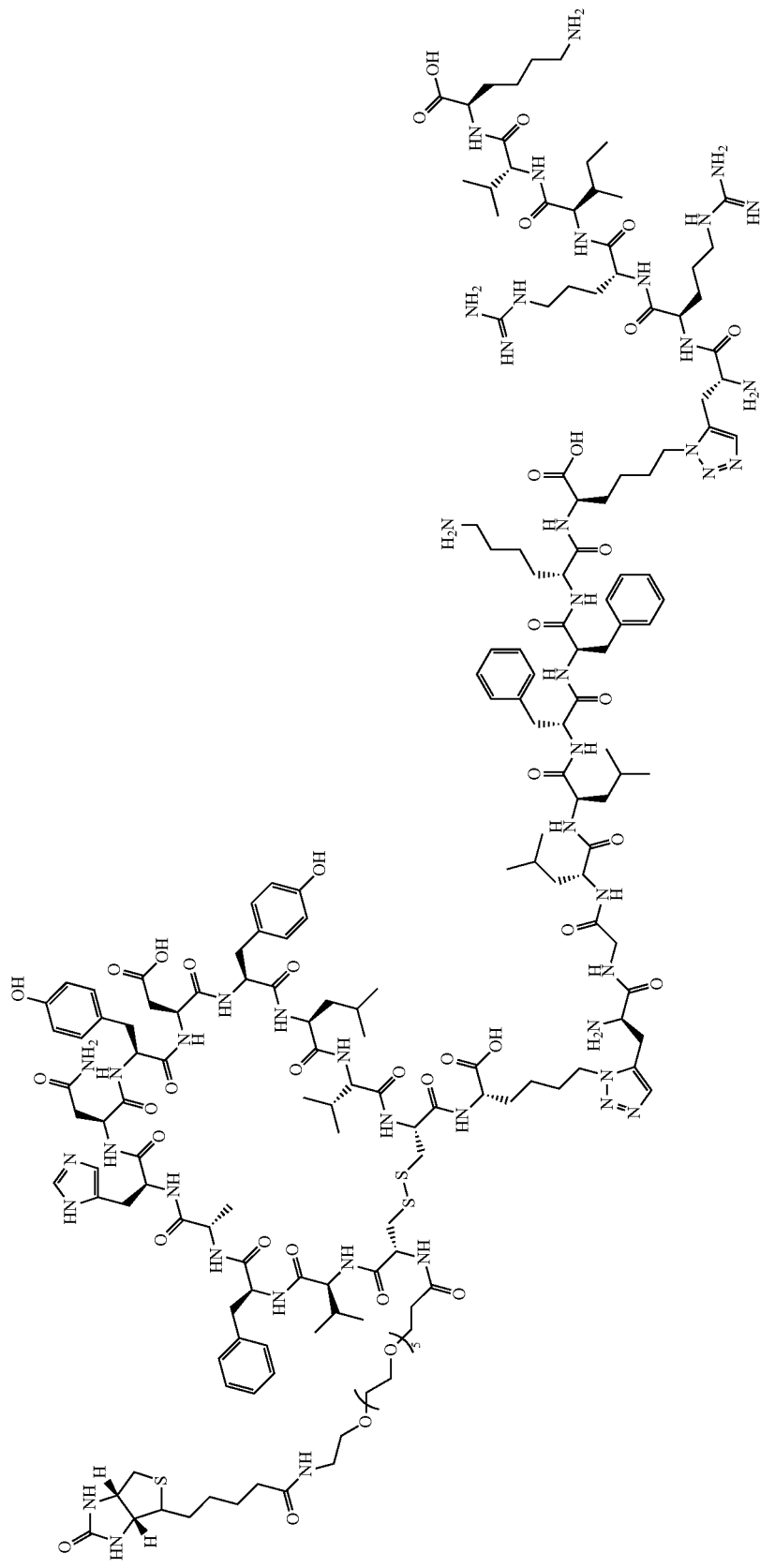

In certain embodiments, a PSA capture agent provided herein is a Tz-4-triligand comprising an anchor ligand, secondary ligand, and tertiary ligand comprising the amino acid sequence set forth in SEQ ID NOs:1, 2, and 4, respectively, and having the structure:
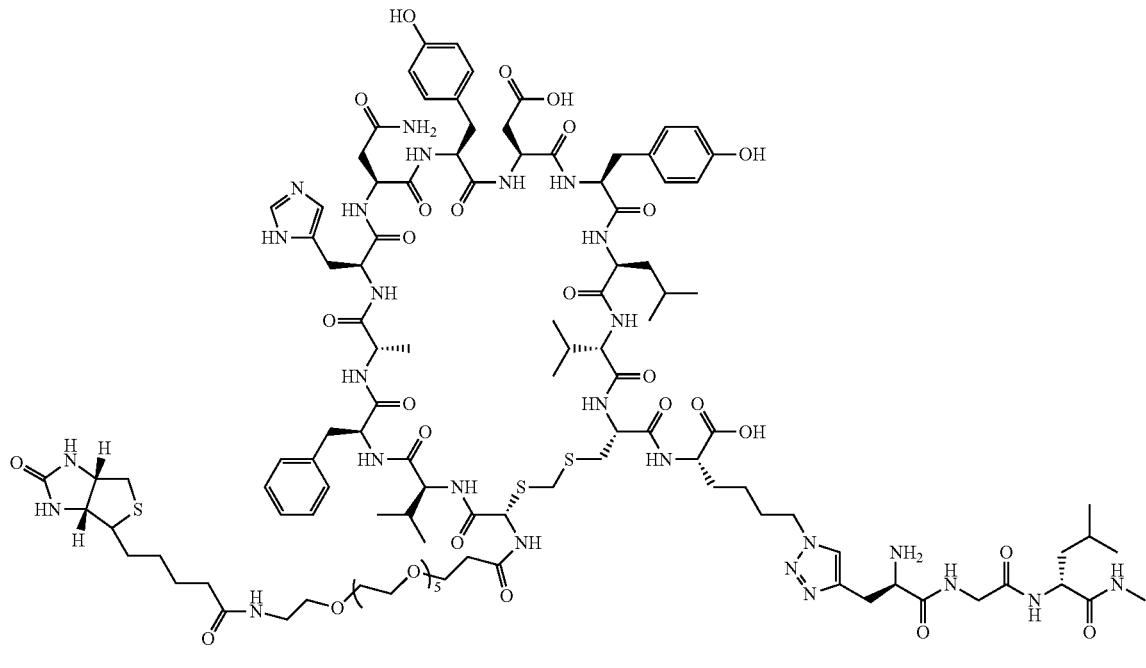
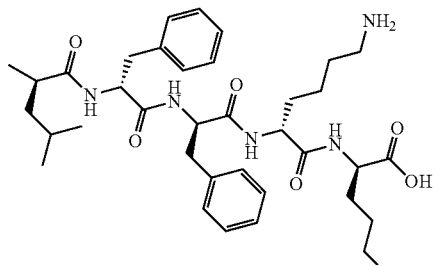
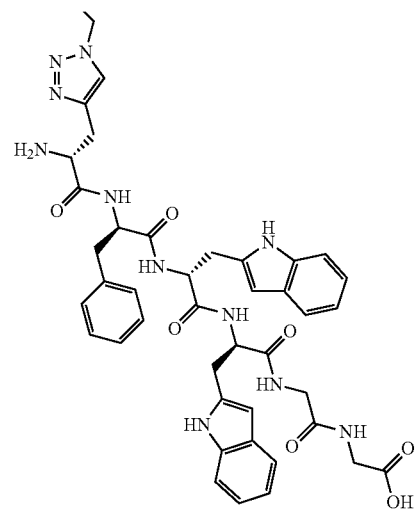

Provided herein in certain embodiments are methods of detecting or quantifying PSA in a sample using the capture agents provided herein. In certain embodiments, these methods comprise an immunoassay where the capture agent substitutes for an antibody, and in certain of these embodiments the immunoassay is a Western blot, pull-down assay, dot blot, or ELISA.

Provided herein in certain embodiments are methods of screening for target-binding moieties for use in the capture agents provided herein.

Provided herein in certain embodiments are methods of synthesizing the capture agents provided herein.

Provided herein in certain embodiments are methods of screening the capture agents provided herein.

Provided herein in certain embodiments are methods of diagnosing and/or staging prostate cancer or a condition associated with elevated PSA levels in a subject using the capture agents provided herein.

Provided herein in certain embodiments are methods of treating prostate cancer or a condition associated with elevated PSA levels in a subject using the capture agents provided herein. In certain of these embodiments, the capture agents provided herein function as immunotherapeutics.

DETAILED DESCRIPTION OF THE INVENTION

Figure 1:
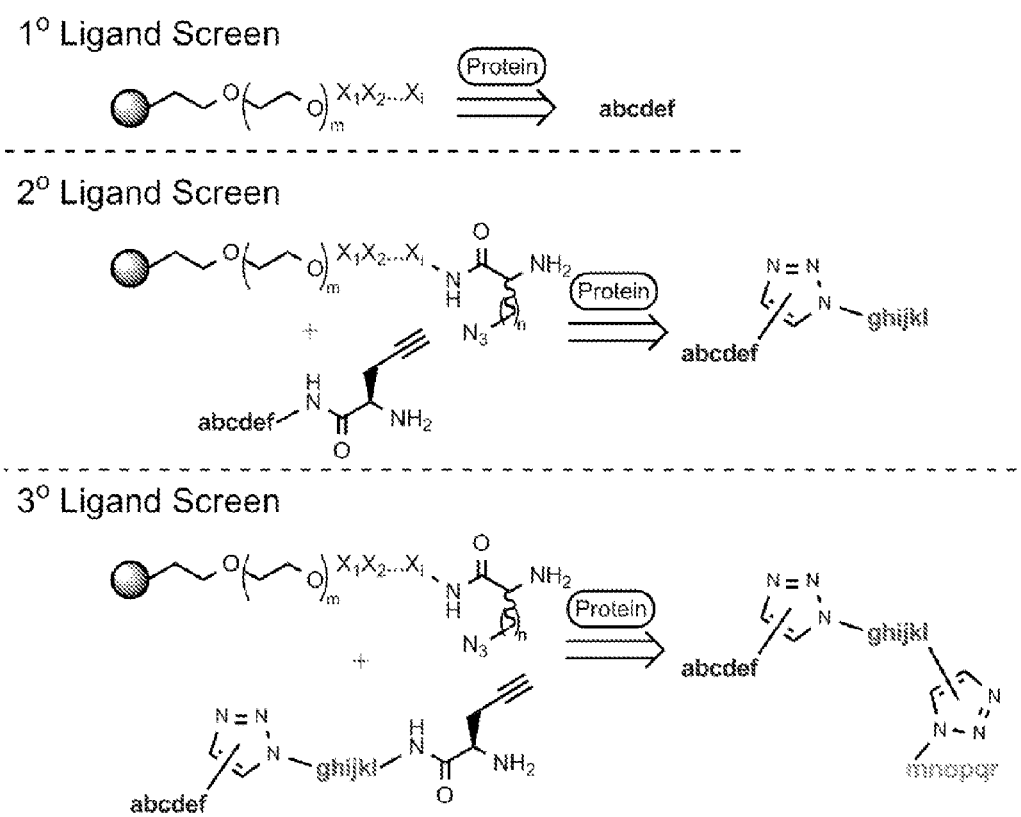
FIG. 1: General capture agent selection scheme.
Figure 2:
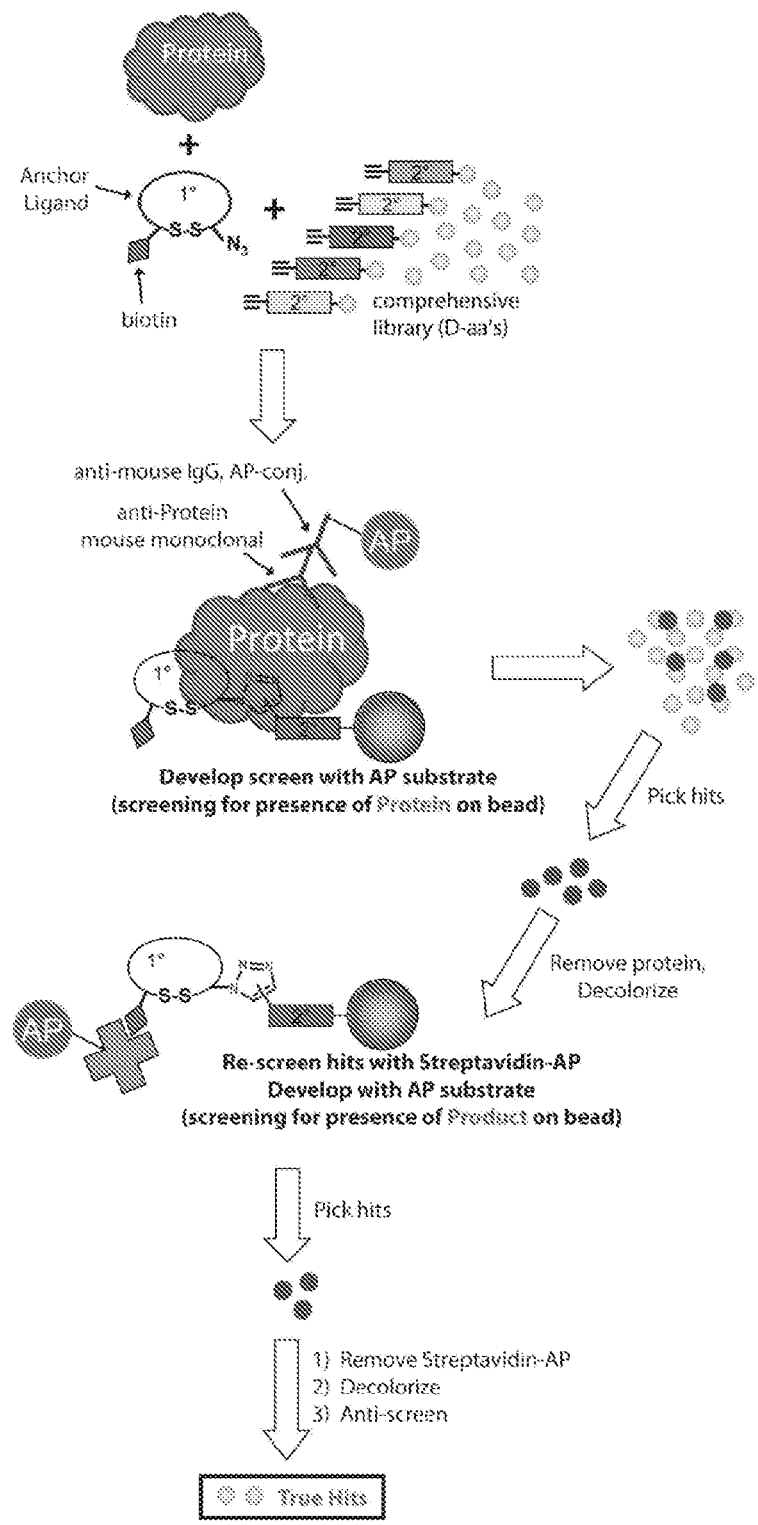
FIG. 2: Selection scheme of a protein capture agent targeting PSA.

Provided herein are protein-catalyzed capture (PCC) agents ("capture agents") that specifically bind one or more target proteins with high affinity and specificity, as well as methods of making and screening these capture agents, methods of using these capture agents in the identification, detection, and/or separation of a target protein, and methods of using these capture agents in the diagnosis, classification, and/or treatment of various conditions. In certain embodiments, the target protein is prostate specific antigen (PSA) or a variation thereof.

The term "capture agent" as used herein refers to a composition that comprises one or more target-binding moieties and which specifically binds to a target protein via those target-binding moieties. Each target-binding moiety exhibits binding affinity for the target protein, either individually or in combination with other target-binding moieties. In certain embodiments, each target-binding moiety binds to the target protein via one or more non-covalent interactions, including for example hydrogen bonds, hydrophobic interactions, and van der Waals interactions. A capture agent may comprise one or more organic molecules, including for example polypeptides, peptides, polynucleotides, and other non-polymeric molecules.

In certain embodiments, a target-binding moiety comprises one or more polypeptides or peptides. In certain of these embodiments, a target-binding moiety comprises one or more peptides comprising D-amino acids, L-amino acids, and/or amino acids substituted with functional groups selected from the group consisting of substituted and unsubstituted alkyl, substituted and unsubstituted azido, substituted and unsubstituted alkynyl, substituted and unsubstituted biotinyl, substituted and unsubstituted azidoalkyl, substituted and unsubstituted polyethyleneglycolyl, and substituted and unsubstituted disubstituted-1,2,3-triazole.

The terms "polypeptide," "peptide," and "protein" are used interchangeably herein to refer to an amino acid sequence comprising a polymer of amino acid residues. The terms apply to amino acid polymers in which one or more amino acid residues is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids, and isomers thereof. Naturally occurring amino acids are those encoded by the genetic code, as well as those amino acids that are later modified, e.g., hydroxyproline, carboxyglutamate, O-phosphoserine, and isomers thereof. The term "amino acid analogs" refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. The term "amino acid mimetics" refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission.

A capture agent comprising two target-binding moieties is referred to herein as a capture agent biligand. In those embodiments where the capture agent is a capture agent biligand, the first target-binding moiety is referred to as an anchor ligand, and the second is referred to as a secondary ligand. In certain embodiments, the anchor ligand and secondary ligand are linked to one via a covalent linkage, including for example an amide bond or a 1,4- or 1,5-disubstituted-1,2,3-triazole linkage as shown below:

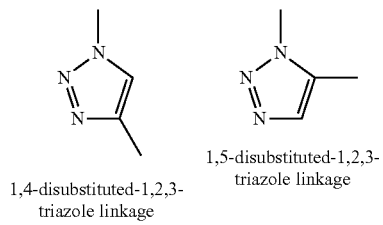

1,4-disubstituted-1,2,3-triazole linkage 1,5-disubstituted-1,2,3-triazole linkage In those embodiments where the anchor and secondary ligands are linked to one another via a 1,5-disubstituted-1,2,3-triazole linkage, the 1,5-disubstituted-1,2,3-triazole may be synthesized in a single chemical reaction using ruthenium catalysis. For example, the 1,5-disubstituted-1,2,3-triazole linkage may be formed using the Ruthenium-Catalyzed Azide/Alkyne Cycloaddition (RuAAC) procedure set forth in FIG. 11. In those embodiments where the anchor and secondary ligands are linked to one another via a 1,4-disubstituted-1,2,3-triazole linkage, the 1,4-disubstituted-1,2,3-triazole linkage may be formed by Cu-Catalyzed Azide/Alkyne Cycloaddition (CuAAC). Other processes may be used that lead to mixtures of 1,4- and 1,5-disubstituted-1,2,3-triazole regioisomers and/or require multiple chemical reactions for exclusive preparation.

In certain embodiments, the anchor and secondary ligands are linked to one another by a Tz5 or Tz4 linkage having the following structures:

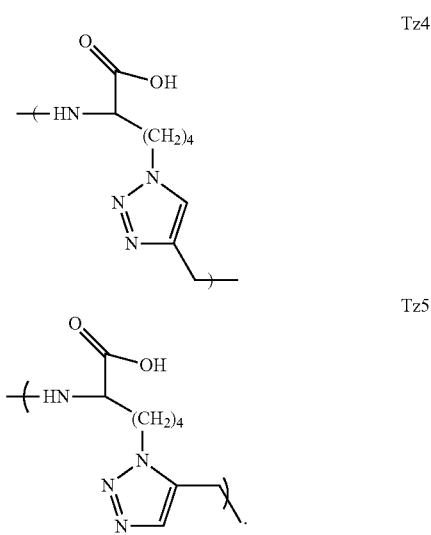

A capture agent comprising three target-binding moieties is referred to herein as a capture agent triligand. In certain embodiments of the capture agent triligands provided herein, the capture agent triligand comprises a capture agent biligand linked to a third target-binding moiety, preferably via the secondary ligand in the capture agent biligand. In these embodiments, the third target-binding moiety is referred to as a tertiary ligand. In certain embodiments, the tertiary ligand is linked to the capture agent biligand by a covalent linkage, and in certain of these embodiments the tertiary ligand and the capture agent biligand are linked to one another by a Tz4 or Tz5 linkage.

In those embodiments wherein one or more of the anchor, secondary, and tertiary ligands are linked to one another via amide bonds, the amide bond may be formed by coupling a carboxylic acid group and an amine group in the presence of a coupling agent (e.g., O-(7-azabenzotriazol-1-yl)-N,N,N', N'-tetramethyluronium hexafluorophosphate (HATU), N-hydroxy-7-aza-benzotriazole (HOAt), or diisopropylethylamine (DIEA) in DMF).

In certain embodiments, the capture agents provided herein are stable across a range of reaction conditions and/or storage times or conditions. A capture agent that is "stable" as used herein maintains the ability to specifically bind to a target protein. In certain embodiments, the capture agents provided herein are more stable than an antibody binding to the same target protein under one or more reaction and/or storage conditions. For example, in certain embodiments the capture agents provided herein are more resistant to proteolytic degradation than an antibody binding to the same target protein.

In certain embodiments, the capture agents provided herein have a shelf-life of greater than six months, meaning that they are stable in storage for greater than six months. In certain of these embodiments, the capture agents have a shelf-life of one year or greater, two years or greater, or more than three years. In certain of these embodiments, the capture agents are stored as a lyophilized powder. In certain embodiments, the capture agents provided herein have a longer shelf-life than an antibody binding to the same target protein.

In certain embodiments, the capture agents provided herein are stable at temperatures ranging from about −80° to about 120° C. In certain of these embodiments, the capture agents are stable within a temperature range of −80° to −40° C.; −40° to −20° C.; −20° to 0° C.; 0° to 20° C.; 20° to 40° C.; 40° to 60° C.; 60° to 80° C.; and/or 80° to 120° C. In certain embodiments, the capture agents provided herein are stable across a wider range of temperatures than an antibody binding to the same target protein, and/or remain stable at a specific temperature for a longer time period than an antibody binding to the same target protein.

In certain embodiments, the capture agents provided herein are stable at a pH range from about 3.0 to about 8.0. In certain embodiments, the range is about 7.0 to about 8.0.

In certain embodiments, the capture agents provided herein are stable in human serum for more than 12 hours. In certain of these embodiments, the capture agents are stable in human serum for more than 18 hours, more than 24 hours, more than 36 hours, or more than 48 hours. In certain embodiments, the capture agents provided herein are stable for a longer period of time in human serum than an antibody binding to the same target protein.

The term "antibody" as used herein refers to a protein of the kind that is produced by activated B cells after stimulation by an antigen and can bind specifically to the antigen promoting an immune response in biological systems. Full antibodies typically consist of four subunits including two heavy chains and two light chains. The term antibody includes natural and synthetic antibodies, including but not limited to monoclonal antibodies, polyclonal antibodies or fragments thereof. Exemplary antibodies include IgA, IgD, IgG1, IgG2, IgG3, IgM and the like. Exemplary fragments include Fab Fv, Fab' F(ab')2 and the like. A monoclonal antibody is an antibody that specifically binds to and is thereby defined as complementary to a single particular spatial and polar organization of another biomolecule which is termed an "epitope." In some forms, monoclonal antibodies can also have the same structure. A polyclonal antibody refers to a mixture of different monoclonal antibodies. In some forms, polyclonal antibodies can be a mixture of monoclonal antibodies where at least two of the monoclonal antibodies binding to a different antigenic epitope. The different antigenic epitopes can be on the same target, different targets, or a combination. Antibodies can be prepared by techniques that are well known in the art, such as immunization of a host and collection of sera (polyclonal) or by preparing continuous hybridoma cell lines and collecting the secreted protein (monoclonal).

In certain embodiments of the capture agents provided herein, the capture agent is a PSA capture agent biligand selected from the group consisting of biotin-PEG$_5$-cyclic (CVFAHNYDYLVC)-Tz5-Gllffk ("PSA-Tz5 BL1," FIG. 3(b); biotin-PEG$_5$-cyclic(SEQ ID NO:1)-Tz5-SEQ ID NO:2) and biotin-PEG$_5$-cyclic(CVFAHNYDYLVC)-Tz-4-Gllffk ("PSA-Tz4 BL1," FIG. 3(d); biotin-PEG$_5$-cyclic(SEQ ID NO:1)-Tz-4-SEQ ID NO:2), where PEG$_5$ represents —(NH—(C2H4-O-)5-C(O))—.

In certain embodiments of the capture agents provided herein, the capture agent is a PSA capture agent triligand selected from the group consisting of biotin-PEG$_5$-cyclic (CVFAHNYDYLVC)-Tz5-Gllffk-Tz5-rrivk ("PSA-Tz5 TL1," FIG. 3(c); biotin-PEG$_5$-cyclic(SEQ ID NO:1)-Tz5-SEQ ID NO:2-Tz5-SEQ ID NO:3) and biotin-PEG$_5$-cyclic (CVFAHNYDYLVC)-Tz-4-Gllffk-Tz-4-fwwgg ("PSA-Tz4 BL1," FIG. 3(d); biotin-PEG$_5$-cyclic(SEQ ID NO:1)-Tz-4-SEQ ID NO:2-Tz-4-SEQ ID NO:4).

In certain embodiments, methods are provided for synthesizing a capture agent as provided herein. In certain embodiments, these methods comprise:

a) preparing a synthesis block of a target-binding moiety, the synthesis block comprising the target-binding moiety and at least one reactive group that can form a desired linkage with another synthesis block, wherein:
   i) the linkage is selected from the group consisting of amide linkage, 1,4-disubstituted 1,2,3-triazole linkage and 1,5-disubstituted-1,2,3-triazole linkage; and
   ii) all other active functional groups of the target-binding moiety are protected to avoid undesired reactions; and
b) coupling the synthesis blocks of the target-binding moieties to provide the capture agent.

In certain embodiments, the capture agent comprises one or more Tz4 and/or Tz5 linkages. Because the Tz4 and Tz5 linkage comprises an amide linkage and a disubstituted 1,2,3-triazole linkage, the synthesis blocks of the Tz4 or Tz5-linked capture agent can be linked through formation of an amide linkage or a catalyzed Azide/Alkyne Cycloaddition.

In certain embodiments, a capture agent may be further modified to obtain a desired chemical or biological activity. Examples of desired chemical or biological activities include, without limitation, improved solubility, stability, bioavailability, detectability, or reactivity. Examples of specific modifications that may be introduced to a capture agent include, but are not limited to, cyclizing the capture agent through formation of a disulfide bond; modifying the capture agent with other functional groups or molecules. Similarly, a capture agent may be synthesized to bind to non-canonical or non-biological epitopes on proteins, thereby increasing their versatility. In certain embodiments, the capture agent may be modified by modifying the synthesis blocks of the target-binding moieties before the coupling reaction.

Also provided herein are methods for screening target-binding moieties and/or preparing capture agents that comprise these target-binding moieties. In certain of these embodiments, the screening/preparation process comprises the following steps:

a) preparing a first plurality of candidate peptides to select an anchor ligand for the target protein;
b) contacting the target protein with the first plurality of candidate peptides;
c) selecting a candidate peptide with affinity for the target protein as the anchor ligand;
d) sequencing the anchor ligand;
e) preparing an anchor ligand selection block comprising the anchor ligand and an azido group or an alkynyl group;
f) preparing a second plurality of candidate peptides to select a secondary ligand for the target protein, the second plurality of peptides comprising an azido group or an alkynyl group if the anchor ligand selection block comprises an alkynyl group and azido group respectively;
g) contacting the anchor ligand selection block and the second plurality of peptides with the target protein;
h) providing a capture agent biligand by forming a disubstituted 1,2,3-triazole linkage between the anchor ligand selection block and the secondary ligand wherein the azido and alkynyl group of the anchor ligand selection block and the secondary ligand are brought in close proximity by binding to the target protein;

i) selecting the capture agent biligand that has an affinity with the target protein;

j) sequencing the secondary ligand; and k) preparing a biligand selection block comprising an azido group or an alkynyl group; and repeating steps f) to k) until a capture agent having desired binding affinity to the target protein is screened.

One or more steps of the screening process may be omitted if one or more ligands are known.

In certain embodiments, the first and/or second plurality of candidate peptides for selection is a "one bead one compound" (OBOC) peptide library, wherein the peptides comprise 5 to 7 D-amino acid residues and coupled with a D-propargylglycine at the N-terminus.

In other embodiments of the screening and preparation methods provided herein, the methods may utilize a known anchor ligand. In these embodiments, the step of anchor ligand screening is omitted. For example, the anchor ligand used for the screening process may be biotin-PEG$_5$-cyclic (CVFAHNYDYLVC) (biotin-PEG$_5$-cyclic(SEQ ID NO:1)). In these embodiments, an azide-modified anchor ligand selection block refers to biotin-PEG$_5$-cyclic(CVFAHNYDYLVC)-Az, wherein Az represents a modified amino acid comprising an azido group (e.g., Az4, wherein Az4 represents L-azidolysine). In these embodiments, the screening/preparation process comprises the following steps:

a) contacting PSA with biotin-PEG$_5$-cyclic(CVFAHNYDYLVC)-Az4 ("azide-modified PSA capture agent anchor ligand selection block (I)") to provide a PSA-anchor complex;

b) contacting the PSA-anchor complex with a first plurality of candidate peptides to select a secondary ligand, the peptides coupled with a D-propargylglycine at its N-terminus;

c) providing a PSA capture agent biligand by forming a 1,5-disubstituted-1,2,3-triazole linkage between the anchor ligand selection block and the secondary ligand, wherein the azido and alkynyl group of the anchor ligand selection block and the secondary ligand are brought in close proximity by binding to the target protein to provide a bead modified with the PSA capture agent biligand;

d) selecting the beads modified with the PSA capture agent biligand;

e) removing the PSA capture agent biligands from the beads modified with the PSA capture agent biligand;

f) sequencing the PSA capture agent secondary ligand of the PSA capture agent biligand;

g) preparing a biotin-PEG$_5$-cyclic(CVFAHNYDYLVC)—PSA secondary ligand-Az4 ("azide-modified capture agent biligand selection block (I)"); and h) repeating the above steps until a PSA capture agent having the properties is identified.

Further provided herein are methods of diagnosing and/or staging prostate cancer or other disorders associated with altered PSA levels using the capture agents provided herein. In certain of these embodiments, the methods comprise (a) obtaining a biological sample from a subject; (b) measuring the presence or absence of PSA in the sample with the PSA capture agent; (c) comparing the levels of PSA to a predetermined control range for PSA; and (d) diagnosing prostate cancer or a prostate disorder based on the difference between levels in the biological sample and the predetermined control.

In certain embodiments, the capture agents provided herein may comprise one or more detection labels, including for example biotin, copper-1,4,7,10-tetraazacyclododecane-1,4,7,10-tetraacetic acid (copper-DOTA), or radiolabeled products that may include gamma emitters, proton emitters, positron emitters, tritium, or covered tags detectable by other methods (i.e. gadolinium) among others.

A capture agent-based protein assay yields highly reproducible results across synthetic preparation of capture agents.

A biological sample for use in the methods provided herein may be selected from the group consisting of organs, tissue, bodily fluids and cells. In another aspect, the bodily fluid is selected from the group consisting of blood, serum, plasma, urine, sputum, saliva, stool, spinal fluid, cerebral spinal fluid, lymph fluid, skin secretions, respiratory secretions, intestinal secretions, genitourinary tract secretions, tears, and milk. In another aspect, the biological sample is a blood sample.

Also provided herein are methods of treating prostate cancer or a condition associated with increased PSA levels by administering one or more of the capture agents disclosed herein. In certain of these embodiments, the capture agents may be linked to one or more additional therapeutic agents, including for example a chemotherapeutic agent.

In certain embodiments, kits are provided that comprise one or more capture agents as disclosed herein. In certain embodiments, these kits may be used for detecting and/or quantifying PSA, and in certain of these embodiments the kits may be used in the diagnosis and/or staging of prostate cancer or other disorders associated with altered PSA levels. In certain embodiments, a kit as provided herein comprises: (a) a substrate comprising an adsorbent thereon, wherein the adsorbent is suitable for binding PSA, and (b) a washing solution or instructions for making a washing solution, wherein the combination of the adsorbent and the washing solution allows detection of PSA. In other embodiments, the kits provided herein may be used in the treatment of prostate cancer or a condition associated with elevated PSA levels.

In certain embodiments, the kits provided herein may further comprise instructions for suitable operational parameters in the form of a label or a separate insert. For example, the kit may have standard instructions informing a consumer/kit user how to wash the probe after a sample of plasma or other tissue sample is contacted on the probe.

In another embodiment, a kit as provided herein comprises (a) PSA capture agents that specifically bind PSA; and (b) a detection reagent. Such kits can be prepared from the materials described herein.

The kits provided herein may optionally comprise a standard or control information, and/or a control amount of material, so that the test sample can be compared with the control information standard and/or control amount to determine if the test amount of PSA detected in a sample is a diagnostic amount consistent with a diagnosis of prostate cancer or other prostate condition.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

EXAMPLES

Example 1

Screening and Preparation of PSA Capture Agent Triligands

Reagents.

Fmoc-D-X—OH (Fmoc, fluoren-9-ylmethoxycarbonyl) (X=Ala, Arg(Pbf) (Pbf, pentamethyldihydrobenzofuran-5-sulfonyl), Asn(Trt) (Trt, trityl), Asp(OtBu) (tBu, tert-butyl), Glu(OtBu), Gln(Trt), Gly, His(Trt), Ile, Leu, Lys(Boc) (Boc, tert-butyloxycarbonyl), Met, Phe, Pro, Ser(tBu), Thr(tBu), Trp(Boc), Tyr(tBu), and Val) (Anaspec; San Jose, Calif.). Amino acid coupling reactions were performed in 1-methyl-2-pyrrolidinone (NMP, 99%) with HBTU (O-Benzotriazole-N,N,N',N'-tetramethyl-uronium-hexafluoro-phosphate; (AAPPTEC) and N,N'-diisopropylethylamine (DIEA). For removal of Nα-Fmoc protecting groups, a solution of 20% piperidine in NMP was used. For final deprotection of the peptide libraries, trifluoroacetic acid (TFA, 98% min. titration) and triethylsilane (TES) were used. All solvents and reagents were purchased from Sigma-Aldrich (St. Louis, Mo.).

Construction of Peptide Libraries.

Randomized OBOC libraries of penta- to heptapeptides (5-7) were synthesized using an automatic synthesizer, Titan 357 (AAPPTEC), via standard split-mix methods on polyethylene glycol-grafted polystyrene beads (TentaGel S—NH2, 90 μm, 0.29 mmol/g, $2.86 \times 10^6$ beads/g). In a typical library construction, non-natural D-stereoisomers were used at each position in the peptide sequence. For the coupling steps, a standard solid-phase peptide synthesis method with Fmoc chemistry (Fields 1990) was used. The resin was swelled in NMP for two hours in the collection vessel (CV). The coupling of Fmoc-methionine was initiated by addition of 0.17 equiv of HATU (2-(7-Aza-1H-benzotriazole-1-yl)-1,1,3,3-tetramethylammonium hexafluorophosphate; ChemPep) and two equivalents of DIEA. The coupling reaction was run for 30 minutes. Following the coupling step, the beads were thoroughly washed (4×NMP) and treated with 20% piperidine in NMP (5 minutes followed by a 15 minute wash with a fresh aliquot of deprotection solution). The resin was thoroughly washed (4×NMP, 4×DCM) and divided into multiple equal-mass aliquots for the next cycle of coupling in the reaction vessel (RV). With the coupling and Fmoc deprotection completed, the resins were combined in the collection vessel. The procedures were repeated until the desired length of peptide was attained. The amino acid side chain protective groups were then removed by incubation in trifluoroacetic acid (94%), water (3%), and triisopropylsilane (3%) for 2 hour. The library resin was then washed thoroughly with dichloromethane (DCM; 5×), methanol (MeOH; 5×), water (5×), MeOH (5×), DCM (5×), and then diethyl ether (5×). The resulting resin was dried under vacuum and stored at 4° C.

Selection was carried out by in situ click chemistry technique, where the target protein acts as the catalyst that conjugates azide to alkyne candidate ligands (Agnew 2009). For the screen, a 200-mg portion of the OBOC library, coupled with D-propargylglycine at the N-terminus, was transferred into an 8-mL capacity Alltech vessel and pre-incubated in a blocking solution consisting of 0.05% $NaN_3$, 0.1% Tween 20, and 0.1% BSA in PBS buffer (pH 7.4), for 1 hour on a 360°-rotator at 25° C. Separately, a 3 mL volume of 50 nM human PSA (free PSA, Scripps Laboratories #P0725) diluted in blocking solution was preincubated with L-azidolysine-modified Anchor Ligand Biotin-(PEG)-5-cyclic(CVFAH-NYDYLVC)-Az4 (Biotin-(PEG)-5-cyclic(SEQ ID NO:1)-Az4; PEG=5× ethylene glycol, Az4=L-azidolysine) (Wu 2000) for 2 hours or a 360°-rotator at 25° C. The Anchor Ligand was supplied at a 2000-fold excess of the protein. After draining the blocking solution from the OBOC library, the pre-incubated solution of 50 nM free PSA and Anchor Ligand was then added to the library resin and incubated for 4 hours on a 360°-rotator at 25° C. (FIG. 1). The screen was washed with 3×5 mL of the blocking solution, and 3 mL of 0.1 μg/mL anti-human PSA mouse monoclonal antibody (PS6, Abcam) was added. After 1 hour incubation at 25° C., the screen was washed with 5×3 mL of the blocking solution. Next, 3 mL of 1:25,000 anti-mouse IgG AP-linked antibody (#7056, Cell Signaling) was presented to the screen and incubated for 1 hour at 25° C., to select for a capture agent biligand which pairs with the PS6 monoclonal for detection of PSA. To eliminate non-specifically bound proteins, the screen was washed with 5×3 mL Blocking Solution, 5×3 mL Wash 1 Buffer (25 mM Tris-Cl, 10 mM $MgCl_2$, 700 mM NaCl, pH 7.5), followed by 5×3 mL wash 2 Buffer (25 mM Tris-Cl, pH 7.5), and drained by vacuum. BCIP:NBT (Promega #S3771), freshly prepared in Alkaline Phosphatase Buffer (100 mM Tris-HCl [pH 9.0], 150 mM NaCl, 1 mM $MgCl_2$), was used to develop the screen. The most intensely colored purple beads ("initial hits") were selected manually. Selected beads were decolorized with 7.5 M guanidine hydrochloride (pH 2.0) to remove bound proteins and antibodies, followed by NMP.

Next, selected beads were pre-incubated in blocking solution to prepare for a second round of screening. After draining the blocking solution from the selected beads, 3 mL of 1:10, 000 AP-linked Streptavidin (Promega) was incubated for 45 min at 25° C. AP-linked Streptavidin distinguished those beads which contain a biotin label, and therefore products of PSA-templated in situ click biligand conjugation. To eliminate non-specifically bound proteins, the screen was washed with 5×3 mL Blocking Solution, 5×3 mL Wash 1 Buffer, followed by 5×3 mL Wash 2 Buffer, and drained by vacuum. BCIP:NBT, freshly prepared in Alkaline Phosphatase Buffer, was used to develop the screen. The most intensely colored beads ("product hits") were selected manually. Selected beads were decolorized with 7.5 M guanidine hydrochloride (pH 2.0) to remove bound proteins. The decolorization was followed by NMP. After both the Initial and Product Screens, anti-screens were separately performed to eliminate beads that displayed non-specific binding to the reagents used to visualize the screen. Following this refinement, sequencing of authentic hits was performed with MALDI-TOF/TOF and a semi-automated algorithm (Lee 2010).

To determine the geometry (1,4-vs. 1,5-) of the triazole in the biligand product formed during the in situ click chemistry screen, biligands containing the 1,4- and 1,5-substituted-1,2, 3-triazole were synthesized individually (see Example 2). Biological assays were performed to determine the biligand with higher affinity and selectivity (see Examples 3-9). Mass spectrometric analysis (e.g., Maldi-TOF/TOF, LC/MS, etc.) was conducted to further confirm the preferred triazole substitution.

Selection of Capture Agent Triligand by In Situ Click Screen.

A 200-mg portion of the OBOC library, coupled with D-propargylglycine at the N-terminus, was transferred into an 8-mL capacity Alltech vessel and pre-incubated in a blocking solution consisting of 0.05% $NaN_3$, 0.1% Tween 20, and 0.1% BSA in PBS buffer (pH 7.4), for 1 hour on a 360°-rotator at 25° C. Separately, a 3 mL volume of 10 nM free PSA diluted in blocking solution was preincubated with L-azidolysine-modified capture agent biligand Biotin-(PEG)-5-cyclic (CVFAHNYDYLVC)-Tz(1,5)-Gllffk-Az4 [Biotin-(PEG)-5-cyclic(SEQ ID NO:1)-Tz(1,5)—SEQ ID NO:2-Az4; Tz(1,5)=disubstituted 1,2,3-triazole] for 2 hours on a 360°-rotator at 25° C. The capture agent biligand was supplied at a 5000-fold excess of the protein. After draining the blocking solution from the OBOC library, the pre-incubated solution of 10 nM free PSA and capture agent biligand was then added to the library resin and incubated for 4 hours on a 360°-rotator at 25° C. After probing with anti-human PSA mouse monoclonal antibody (PS6) and anti-mouse IgG AP-linked antibody, initial hits were selected as described. A second round of screening with AP-linked Streptavidin was performed as described. Anti-screens were also separately performed. Following these refinements, sequencing of authentic hits was performed with MALDI-TOF/TOF and a semi-automated algorithm (Lee 2010).

To determine the geometry (1,4-vs. 1,5-) of the triazole formed during the in situ click chemistry screen, triligands containing the 1,4- and 1,5-substituted-1,2,3-triazole were synthesized individually (see Example 2). Biological assays were performed to determine the triligand with higher affinity and selectivity (see Examples 3-9). Mass spectrometric analysis (e.g., Maldi-TOF/TOF, LC/MS, etc.) was conducted to further confirm the preferred triazole substitution.

Figure 3:
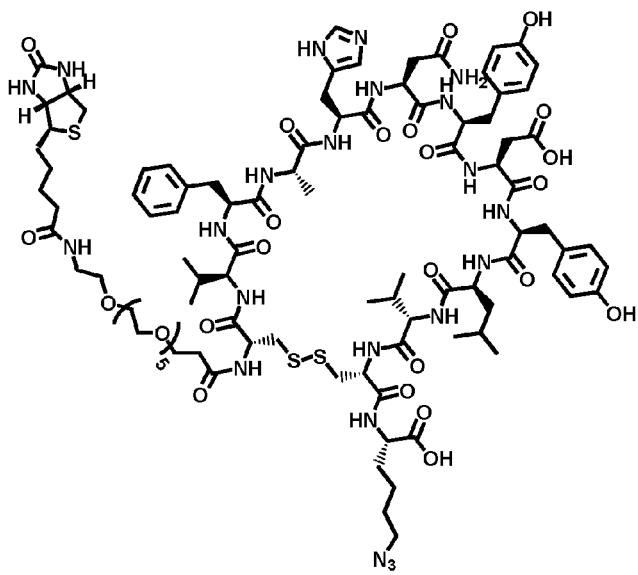
FIG. 3: Chemical structures of protein capture agent targeting PSA a) PSA anchor ligand (SEQ ID NO:1) selection block; b) PSA Tz5-biligand (SEQ ID NOs:1 and 2) selection block; c) PSA Tz5-triligand (SEQ ID NOs:1, 2, and 3); d) PSA Tz-4-biligand (SEQ ID NOs:1 and 2) selection block; and e) PSA Tz-4-triligand (SEQ ID NOs:1, 2, and 4).
Figure 3:
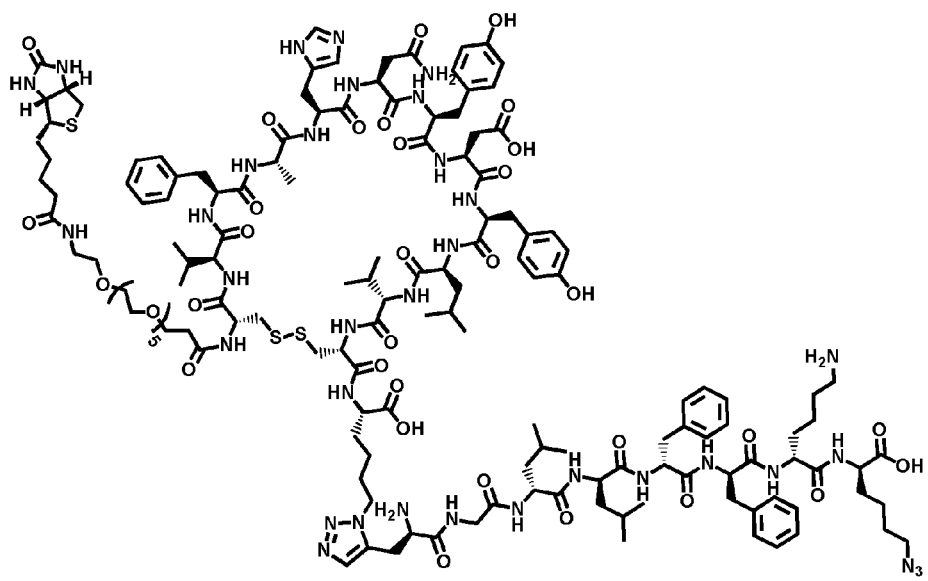
Figure 3:
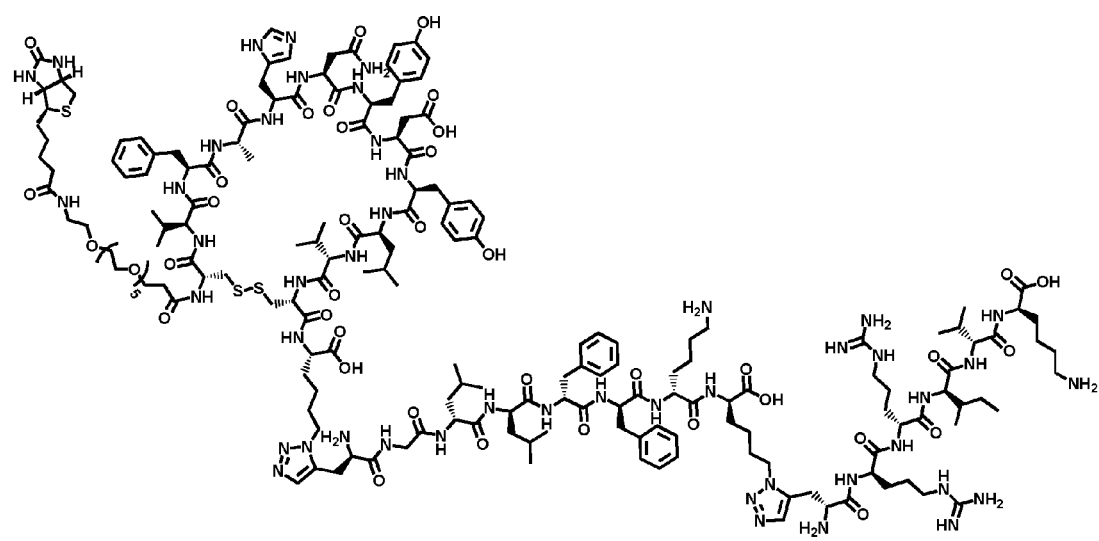
Figure 3:
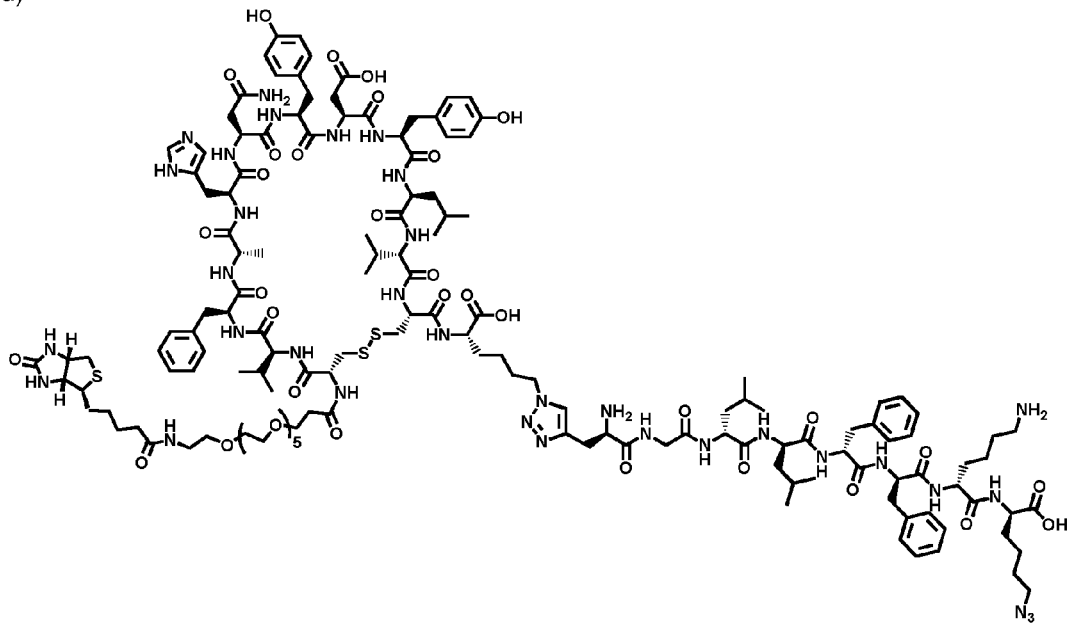
Figure 3:
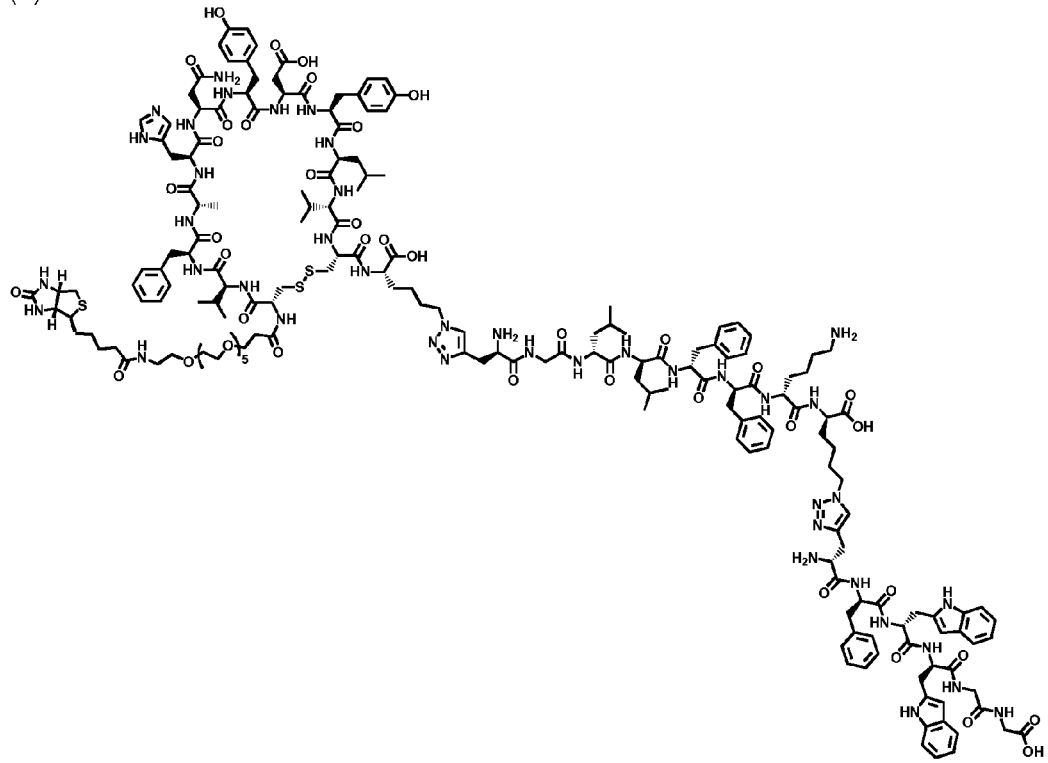

The structures of the Anchor Ligand, Biligand, and Triligand Biotin-(PEG)-5-cyclic(CVFAHNYDYLVC)-Tz(1,5)-Gllffk-Tz(1,5)-rrivk (Biotin-(PEG)-5-cyclic(SEQ ID NO:1)-Tz(1,5)—SEQ ID NO:2-Tz(1,5)—SEQ ID NO:3) are shown in FIG. 3.

CNBr Cleavage of Peptides from Single Beads.

A single bead was transferred to a microcentrifuge tube containing pure water (10 μL). After addition of CNBr (10 μL, 0.50 M in 0.2 N HCl solution) the reaction vessel was purged with argon for 15 minutes and placed under microwave for 1 minute (Lee 2008). After additional purging by argon for 15 minutes the resulting solution was concentrated under centrifugal vacuum for 10 minutes at 45° C. and then for 50 min at 60° C.

MALDI-MS and MS/MS Analysis of Peptides Cleaved from Single Beads.

To each tube were added α-cyano-4-hydroxycinnamic acid CHCA (10 μL, 0.5% matrix solution in acetonitrile/water (70:30)) and acetonitrile/water (10 μL, 70:30 containing 0.1% trifluoroacetic acid (v/v)). A 2-μL volume of the mixture solution was taken up to be spotted onto a 384-well MALDI plate, which was allowed to stand for 15 min to dry naturally.

Example 2

Large-Scale Synthesis of PSA Capture Agent Triligands

Figure 4:
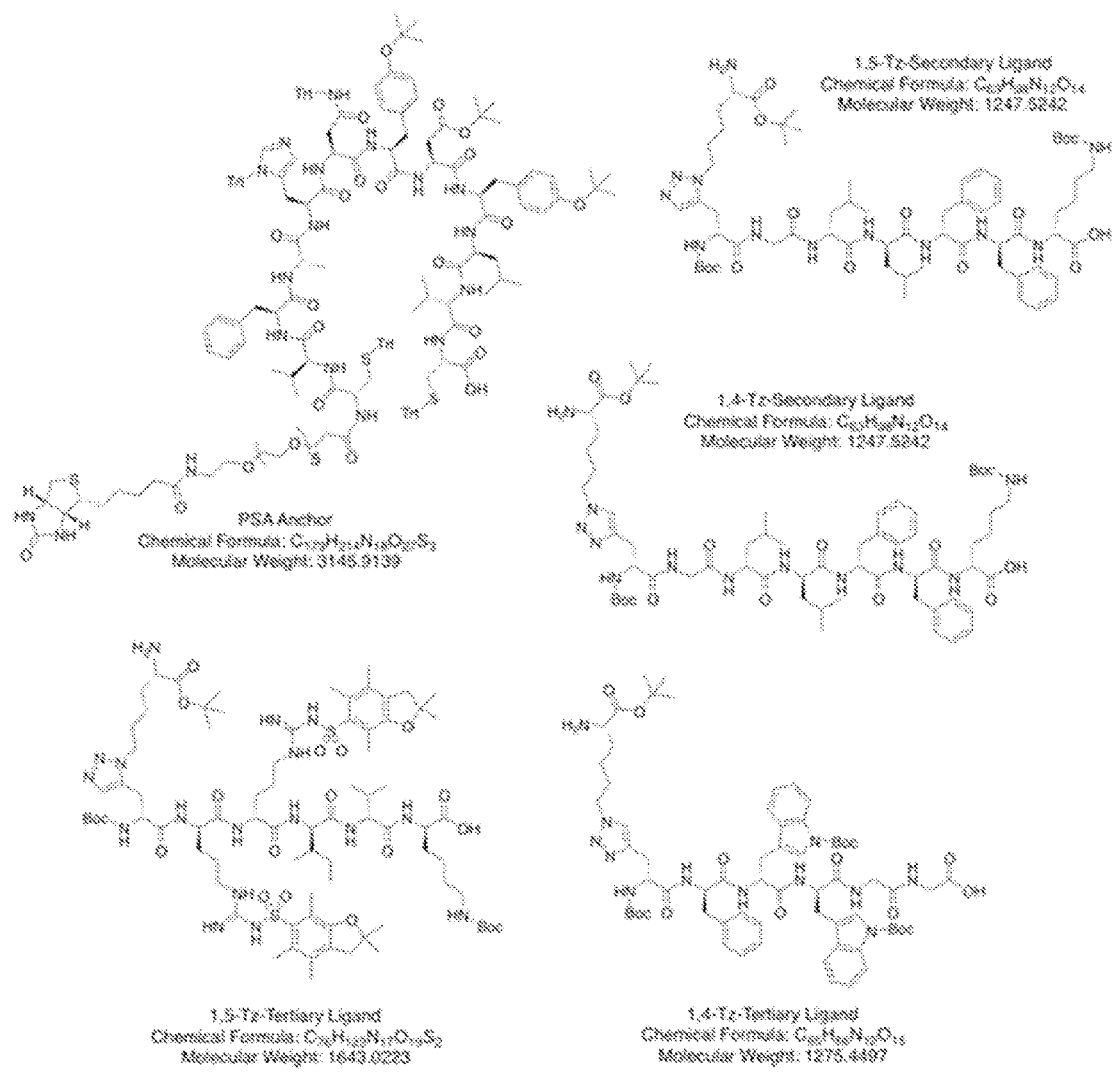
FIG. 4: Chemical structures of a PSA anchor ligand comprising SEQ ID NO:1 (PSA Anchor), PSA Tz5-secondary ligand comprising SEQ ID NO:2 (1,5-Tz-Secondary Ligand), PSA Tz5-tertiary ligand comprising SEQ ID NO:3 (1,5-Tz-Tertiary Ligand), PSA Tz4 secondary ligand comprising SEQ ID NO:2 (1,4-Tz-Secondary Ligand), and PSA Tz-4-tertiary ligand comprising SEQ ID NO:4 (1,4-Tz-Tertiary Ligand). Each ligand is the side chain protected product of Fmoc-based solid-phase peptide synthesis (SPPS) on an AAPPTEC Titan 357 synthesizer.

After selection of the PSA triligand from the in situ click chemistry protocol, large-scale production of material was required for further biological evaluation. In brief, the individual peptide ligands (FIG. 4) were prepared on 2-chlorotrityl chloride (CTC) resin using Fmoc-based solid-phase peptide synthesis (SPPS) on an AAPPTEC Titan 357 synthesizer. Each amino acid coupling reaction incorporated 4 equiv of Fmoc-amino acid, 3.9 equiv of HBTU (O-Benzotriazole-N,N,N',N'-tetramethyl-uronium-hexafluoro-phosphate), and 10 equiv of DIEA. Deprotection of the Fmoc group required 20% piperidine/NMP. The biotin, PEG-chain (n=5) and 1,5-triazole linkers were manually coupled to the peptide fragments on resin. The peptides were cleaved from the resin [dichloromethane/trifluoroethanol/acetic acid (7:3:1)] with side chain protecting groups intact to assure efficient synthesis of subsequent biligand and triligand compounds without unwanted side reactions or products.

Figure 5:
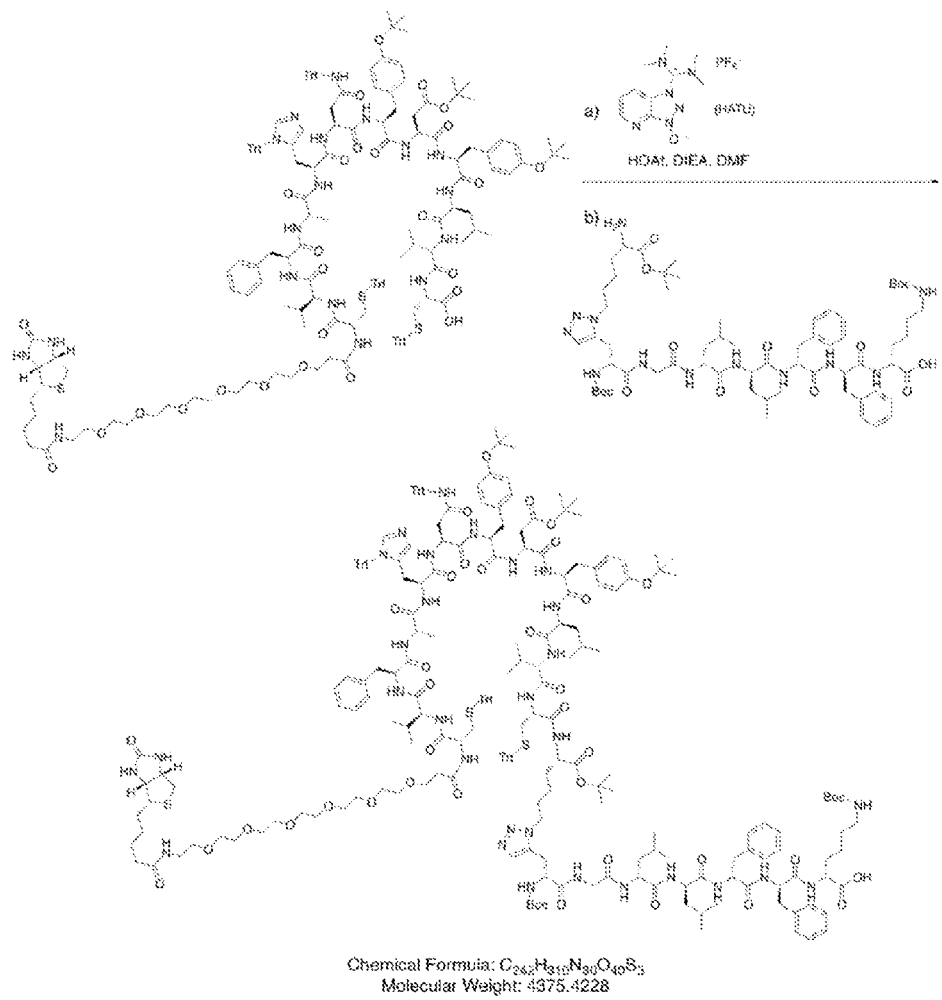
FIG. 5: Synthesis of PSA Tz5-biligand comprising SEQ ID NOs:1 and 2 by coupling a PSA anchor to PSA Tz5-secondary ligand. Each ligand is side chain protected.

As shown in FIG. 5, activation of the C-terminus carboxylic acid of the biotin-PEG-PSA anchor under HATU/HOAt conditions allowed for coupling to the N-terminus of the secondary ligand (1,5-Tz-Gllffk). The crude material from this reaction was carried onto the next step shown in FIG. 6. Again, HATU/HOAt activation of the C-terminus carboxylic acid of the PSA biligand was employed for couple to the tertiary ligand (1,5-Tz-rrivk). Global side-chain deprotection, disulfide formation and purification (FIG. 7) provided the final PSA triligand for further evaluation.

Preparation of the 1,5-triazole linker is illustrated in FIGS. 8-11.

Figure 12:
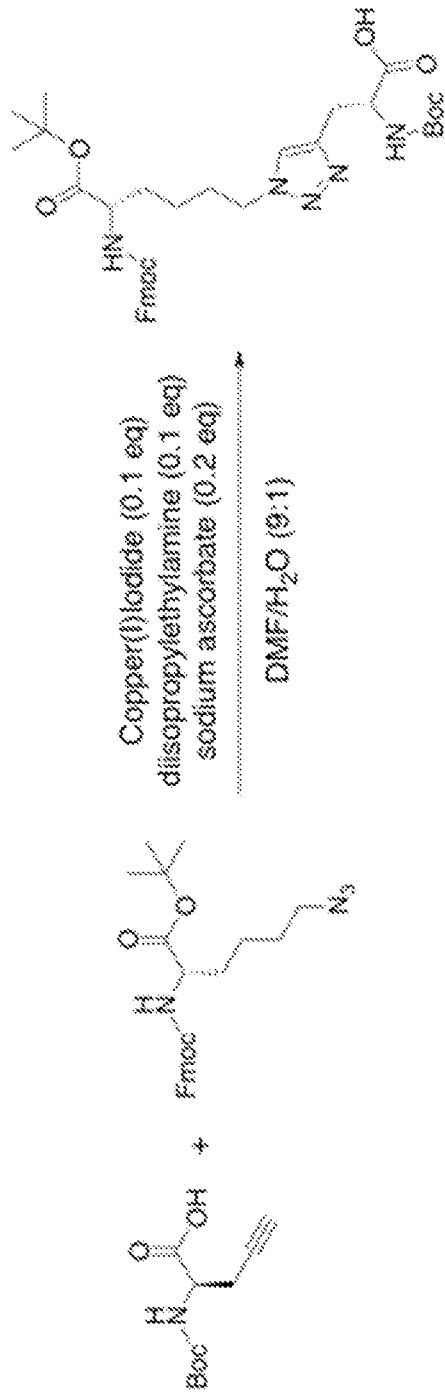
FIG. 12: Copper catalyzed azide/alkyne cycloaddition (CUAAC) between a fully protected alkyne containing amino acid and a fully protected azide containing amino acid to provide a protected 1,4-triazole linked dipeptide according to an embodiment of the disclosure.

Preparation of the 1,4-triazole linker is illustrated in FIG. 12.

Experimental Procedures for PSA Triligand Synthesis

Peptides were synthesized by standard solid-phase Merrifield peptide synthesis using Fmoc-chemistry. Disubstituted 1,2,3-triazole linker comprising Fmoc-L-azidolysine t-butyl ester and Boc-D-Pra-OH was synthesized by Ru-catalyzed azide-alkyne cycloaddition (RuAAC) as previously described (Boren 2008).

Synthesis of PSA Capture Agent Triligand Fragments.

The side chain protected anchor, secondary and tertiary peptide ligands (FIG. 3) were prepared using Fmoc-based solid-phase peptide synthesis (SPPS) on an AAPPTEC Titan 357 synthesizer. Each coupling reaction incorporated 4 equiv of Fmoc-amino acid, 3.9 equiv of HBTU (O-Benzotriazole-N,N,N',N'-tetramethyl-uronium-hexafluoro-phosphate), and 10 equiv of DIEA. The biotin, PEG-chain (n=5) and 1,5-triazole linkers were manually coupled to the peptide fragments.

Reagents (abbreviations). Fmoc=fluoren-9-ylmethoxycarbonyl), Pbf=pentamethyldihydrobenzofuran-5-sulfonyl, Trt=trityl, tBu=tert-butyl, Boc=tert-butyloxycarbonyl), Bn=benzyl, HATU=(2-(7-Aza-1H-benzotriazole-1-yl)-1,1,3,3-tetramethylammonium hexafluorophosphate) (AK Scientific; Union City, Calif.), HOAt=(7-aza-1-hydroxybenzotriazole) (AK Scientific; Union City, Calif.), DMF=dimethylformamide, DIEA=N,N'-diisopropylethylamine (DIEA), TFA=trifluoroacetic acid, TES=triethylsilane. All solvents and reagents were purchased from Sigma-Aldrich (St. Louis, Mo.) unless otherwise noted.

Synthesis of Side-Chain-Protected PSA Tz5-Biligand (FIG. 5):

To a 20 mM solution of biotin-PEG$_5$-(protected)PSA anchor in DMF cooled in a 0° C. ice bath was added 1 equivalent of O-(7-azabenzotriazol-1-yl)-N,N,N',N'-tetramethyluronium hexafluorophosphate (HATU) as a 0.4 M solution in DMF, followed by 1 equivalent of N-hydroxy-7-azabenzotriazole (HOAt) and then 1 equivalent of diisopropylethylamine (DIEA), each as 0.4 M solutions in DMF. A 20 mM solution of Fmoc deprotected secondary ligand in DMF was prepared and added dropwise to the reaction mixture. The reaction was stirred at room temperature for 16 h. The coupled biligand was precipitated with H$_2$O in a tube and centrifuged. The supernatant was removed and the remaining white solid was dried and carried on to the next step as is.

Figure 6:
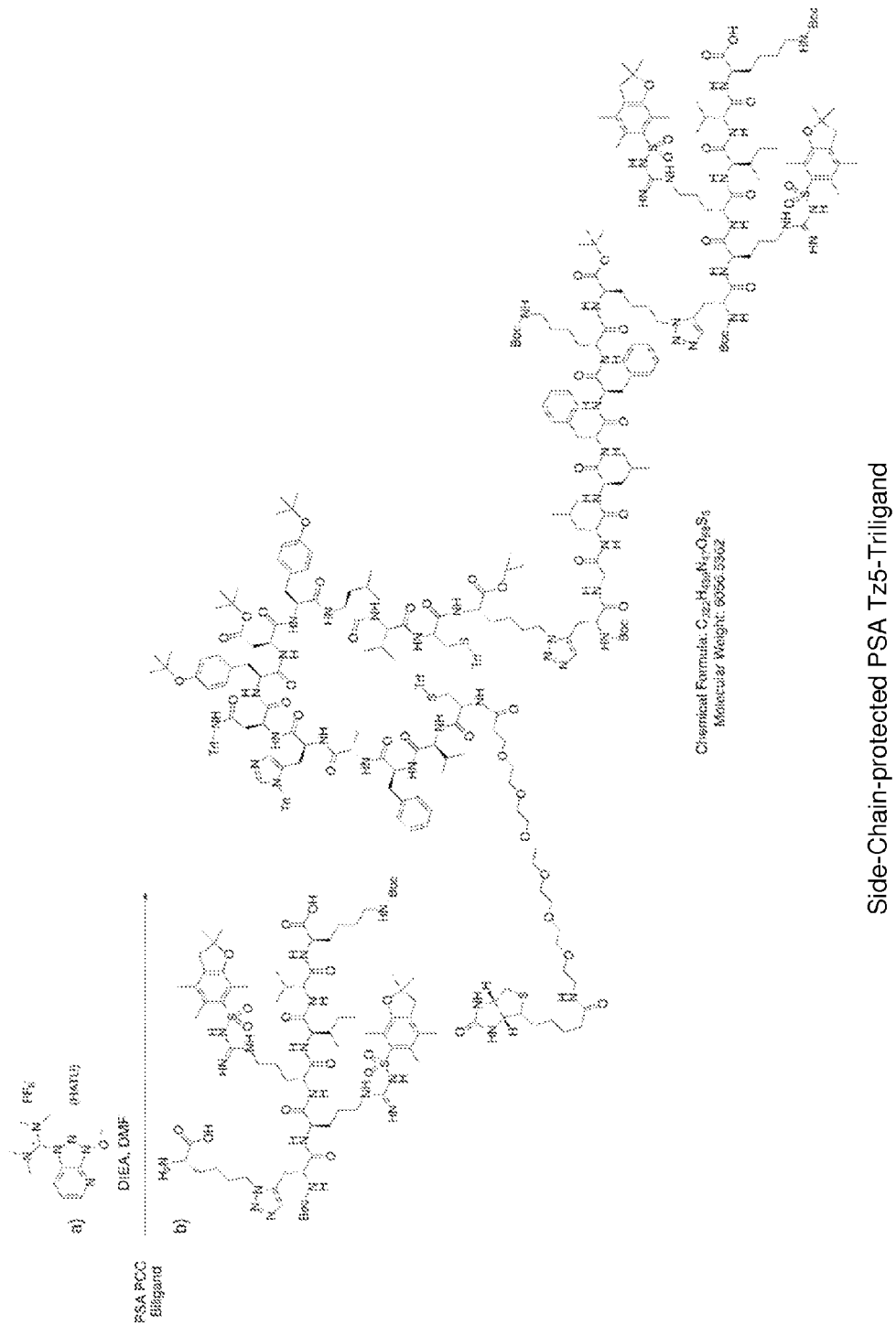
FIG. 6: Synthesis of PSA Tz5-triligand comprising SEQ ID NOs:1, 2, and 3 by coupling PSA Tz5-biligand to a PSA Tz5-tertiary ligand. Each ligand is side chain protected.

Synthesis of Side-Chain-Protected PSA Tz5-Triligand (FIG. 6).

To a 20 mM solution of biotin-PEG$_5$-(protected)PSA biligand in DMF cooled in a 0° C. ice bath was added 1 equivalent of HATU as a 0.4 M solution in DMF, followed by 1 equivalent of HOAt as a 0.4 M solution in DMF and then 1 equivalent of DIEA as a 0.4 M solution in DMF. A 20 mM solution of Fmoc deprotected tertiary ligand in DMF was prepared and added dropwise to the reaction mixture. The reaction was stirred at room temperature for 16 h. The coupled triligand was precipitated with H$_2$O in a tube and centrifuged. The supernatant was removed and the remaining white solid was dried and carried on to the next step as is.

Figure 7:
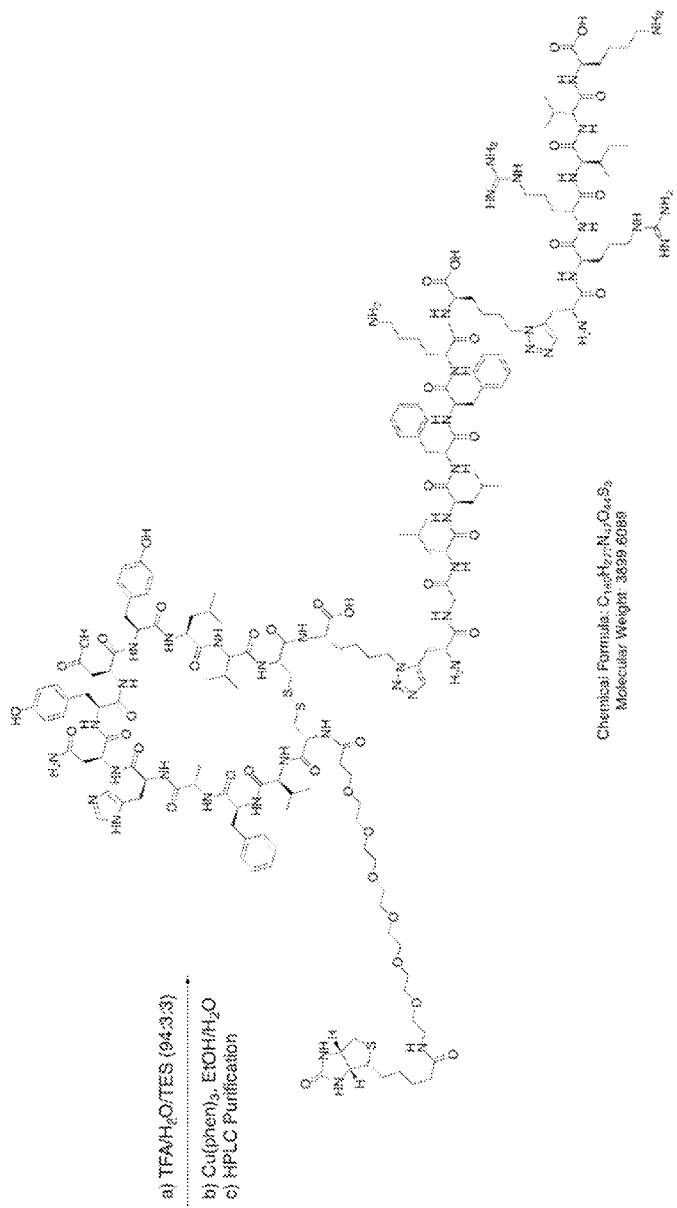
FIG. 7: Synthesis of a PSA Tz5-triligand comprising SEQ ID NOs:1, 2, and 3.

Side-Chain Deprotection and Disulfide Cyclization to PSA Tz5-Triligand (FIG. 7).

Crude white precipitate of side-chain protected triligand was dissolved in trifluoroacetic acid/H$_2$O/triethylsilane (94:

3:3) and stirred at rt for 3 h. The solvents were removed in vacuo. The deprotected triligand was precipitated by the addition of ether. After centrifugation and removal of the supernatant, the remaining white solid was dried and carried on to the next step.

The deprotected triligand was dissolved in minimal DMSO to which a solution of copper(II)phenanthroline [Cu(phen)3] in EtOH/H$_2$O (4:1) was added. The reaction mixture was stirred at room temperature for 24 h then subjected to semi-preparative HPLC purification using a C18 column and a linear gradient of 25→40% B over 120 min, where A=H$_2$O+ 0.1% TFA and B=ACN+0.1% TFA.

Synthesis of the 1,5-Triazole Linker.

Figure 8:
FIG. 8: Preparation of a fully protected alkyne containing amino acid according to an embodiment of the disclosure.

Synthesis of Boc-(D)-propargyl glycine benzyl ester (FIG. 8).

A solution of Boc-(D)-propargylglycine (2.13 g, 10.0 mmol) in dichloromethane (28.0 mL) was cooled in a 0° C. ice bath. To this solution was added 1-ethyl-3-[3-dimethylaminopropyl]carbodiimide hydrochloride [EDAC] (2.25 g, 11.4 mmol) followed by benzyl alcohol (2.0 mL, 19.3 mmol) then dimethylaminopyridine (125 mg, 1.0 mmol). The reaction mixture was stirred and the ice bath was allowed to warm to room temperature. After 3 h, TLC (5% MeOH in DCM, stained with ninhydrin) indicated no Boc-(D)-propargylglycine starting material. The reaction was diluted with H$_2$O (10 mL) and dichloromethane (10 mL). The organic layer was separated and washed with saturated aqueous sodium bicarbonate (2×10 mL) and brine (10 mL). The organic layer was dried over magnesium sulfate and concentrated. Flash chromatography (9:1 then 3:1, Hex/EtOAc) gave the desired benzyl ester product 1.9 g (6.3 mmol, 63% yield) as an oil.

Figure 9:
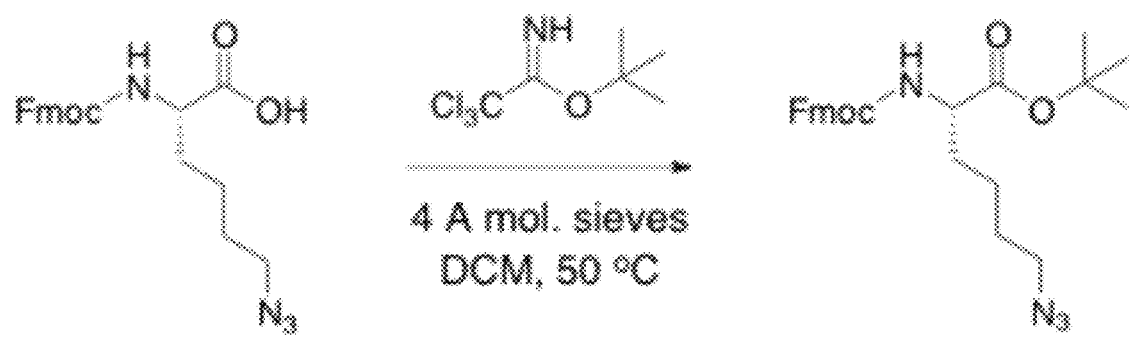
FIG. 9: Preparation of a protected azide containing amino acid according to an embodiment of the disclosure.

Synthesis of Fmoc-(L)-azidolysine t-butyl ester (FIG. 9).

Fmoc-(L)-azidolysine (2.23 mg, 5.65 mmol) was dissolved in dichloromethane (28 mL). To this solution was added 4 Å molecular sieves followed by t-butyl-2,2,2-trichloroacetimidate (1.52 mL, 8.49 mmol). The reaction mixture was heated to 50° C. and stirred for 20 min than an additional 1.52 mL (8.49 mmol) of t-butyl-2,2,2-trichloroacetimidate was added. The reaction was stirred at 50° C. for 16 h. The heterogeneous solution was cooled to 0° C., then filtered to remove the sieves and white precipitate. Cold dichloromethane was used to wash the solid. The resulting solution was washed with saturated sodium bicarbonate and brine. The organic layer was dried over magnesium sulfate and concentrated. Flash chromatography (2% MeOH/DCM) gave the desired t-butyl ester derivative 1.21 g (2.69 mmol, 48% yield) as an oil.

Figure 10:
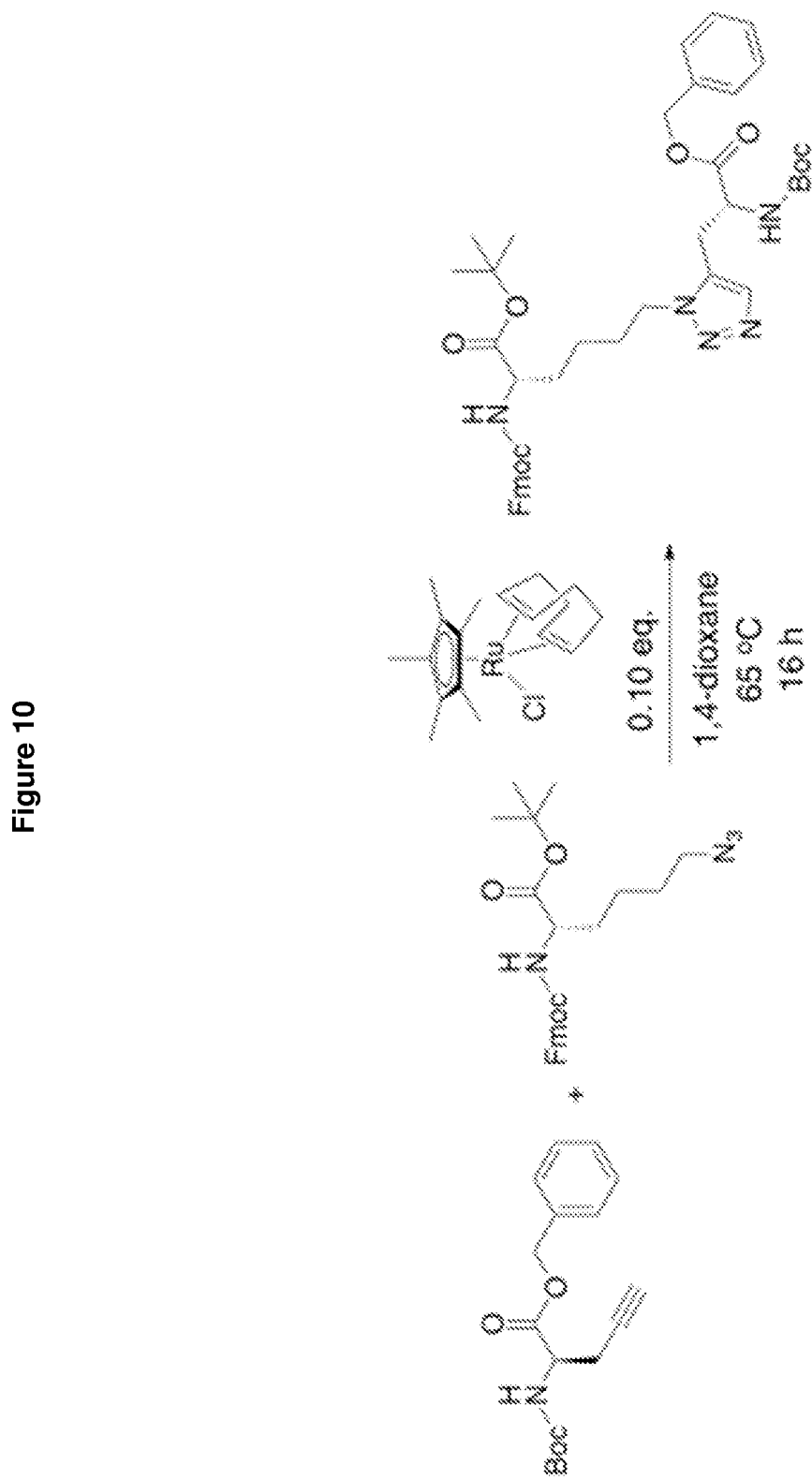
FIG. 10: Ruthenium catalyzed azide/alkyne cycloaddition (RUAAC) between a fully protected alkyne containing amino acid and a fully protected azide containing amino acid to provide a protected 1,5-triazole linked dipeptide according to an embodiment of the disclosure.

Ruthenium-Catalyzed Azide/Alkyne Cycloaddition (RuAAC) Procedure for 1,5-Tz Linker (FIG. 10).

Boc-(D)-propargylglycine benzyl ester (596 mg, 1.96 mmol) was dissolved in anhydrous 1,4-dioxane (3 mL) under Ar. To this solution was added chloro(1,5-cyclooctadiene)(pentamethyl-cyclopentadienyl)ruthenium(II) [65 mg, 0.17 mmol] and the mixture turned a dark reddish-brown color. Fmoc-Lys(N$_3$)-Ot-Bu (798 mg, 1.77 mmol) in anhydrous 1,4-dioxane (3 mL+2 mL washing) was then added and the reaction vial was sealed. The red-brown mixture was heated in a 65° C. oil bath and stirred for 16 h. (Caution should be taken when heating a solution in a sealed vessel.) TLC (1:1 Hex/EtOAc) indicated 1,5-triazole product and no azide starting material. The reaction mixture was cooled to ambient temperature and concentrated to give a dark brown crude material that was immediately purified by flash chromatography (1:1, Hex/EtOAc) providing an off-white solid (1.02 g, 1.4 mmol, 68% yield).

Figure 11:
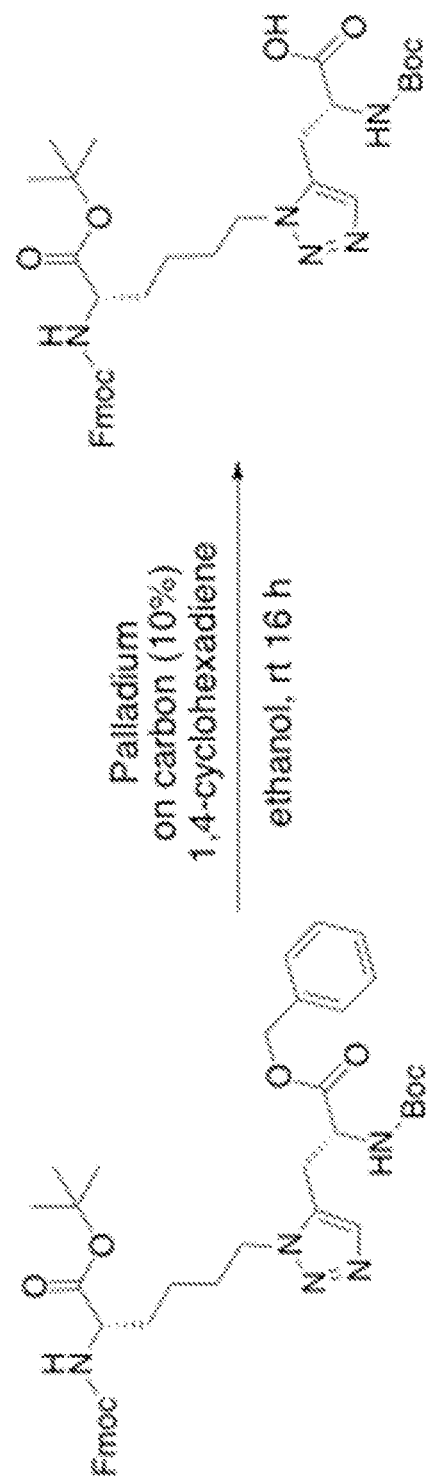
FIG. 11: Deprotection reaction selectively removed a benzyl ester protecting group of a protected 1,5-triazole linked dipeptide according to an embodiment of the disclosure.

Benzyl Ester Deprotection (FIG. 11).

To a solution of 1,5-triazole benzyl ester (442 mg, 0.586 mmol) in ethanol (6.0 mL) was added 10% palladium on carbon (580 mg, 0.058 mmol) followed by 1,4-cyclohexadiene (0.5 mL, 5.3 mmol). The reaction was stirred at room temperature for 16 h then filtered through a pad of celite. The filtrate was concentrated and the resulting crude oil was purified by flash chromatography (5%-10% MeOH in DCM) providing an off-white solid (350 mg, 0.53 mmol, 90% yield).

Copper-Catalyzed Azide/Alkyne Cycloaddition (CuAAC) Procedure for 1,4-Tz Linker (FIG. 12): Fmoc-(L)-Lys(N$_3$)-Ot-Bu (950 mg, 2.1 mmol) and Boc-(D)-propargylglycine (451 mg, 2.1 mmol) were dissolved in a 9:1 mixture of DMF/H$_2$O (7 mL). Copper(I)iodide (42 mg, 0.22 mmol) was added followed by diisopropylethylamine (36 µL, 0.22 mmol). Sodium ascorbate (87 mg, 0.44 mmol) was dissolved in H$_2$O (0.5 mL) and this aqueous solution was added to the reaction mixture. The reaction was stirred for 16 hours. TLC (10% MeOH in DCM) indicated the presence of 1,4-triazole product and no propargylglycine starting material. The reaction mixture was diluted with EtOAC (35 mL) and sat. aq. NaHCO$_3$ (25 mL). The aqueous layer was extracted with EtOAC (3×10 mL). The combined organic layers were washed with 0.1 M ammonium citrate (20 mL) followed by brine (10 mL) then dried over MgSO$_4$, filtered and concentrated to give an oily solid. Purification by flash chromatography (5% to 10% MeOH in DCM) provided a white solid residue (1.3 g, 1.9 mmol, 93% yield).

Example 3

Comparison of Synthetic PSA Capture Agent to a Commercial PSA Antibody (ELISA)

Materials and Methods.

MAXISORP™ microtiter plates were coated with anti-human PSA (PS6, Abcam) at 10 µg/mL in PBS pH 7.4 for 2 hours at room temperature. After washing each microwell with PBS (3×), the plate was filled with 5% non-fat dry milk in TBS (25 mM Tris, 150 mM NaCl, pH 7.25) and blocked for 2 h at room temperature. Serially diluted free PSA (Scripps Laboratories #P0725) in 1% BSA in TBS was incubated across the microtiter plate for 2 h at room temperature. The plate was washed with 1% BSA in TBS (5×), and then 2 µM biotinylated capture agent in 1% BSA in TBS+0.1% DMSO (v/v) was incubated for 1 hour at room temperature. After washing all microwells with 1% BSA in TBS (5×), 0.1 µg/mL Streptavidin Poly-HRP conjugate (Pierce, Ill.) in 1% BSA in TBS was incubated for 30 min at room temperature. The plate was washed with 1% BSA in TBS (10×), followed by TBS (2×), and then developed by adding QuantaRed™ Enhanced Chemifluorescent HRP Substrate (Pierce, Ill.). Using an excitation wavelength of 535 nm, fluorescent emission at 595 nm was recorded by Beckman Coulter DTX880 photometer (Brea, Calif.) as a function of target concentration. The titration curves were fit using a four-parameter regression curve fitting program (Origin 8.5, Northampton, Mass.). Assays were performed in triplicate.

Results and Discussion.

Figure 13:
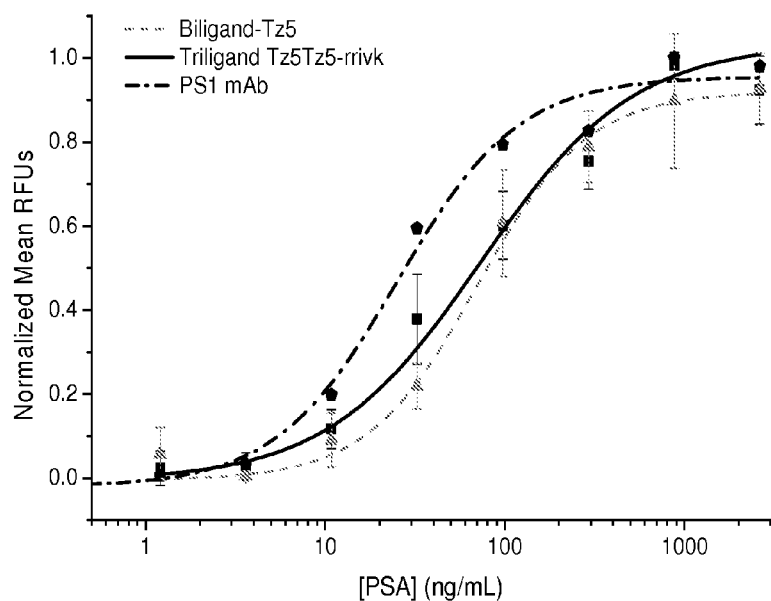
FIG. 13: Sandwich ELISA results of PSA capture agent triligand Tz5Tz5-rrivk, PSA capture agent biligand Tz5 and commercial monoclonal antibody anti-human PSA (PS1 mAb) according to an embodiment of the disclosure.
Figure 14:
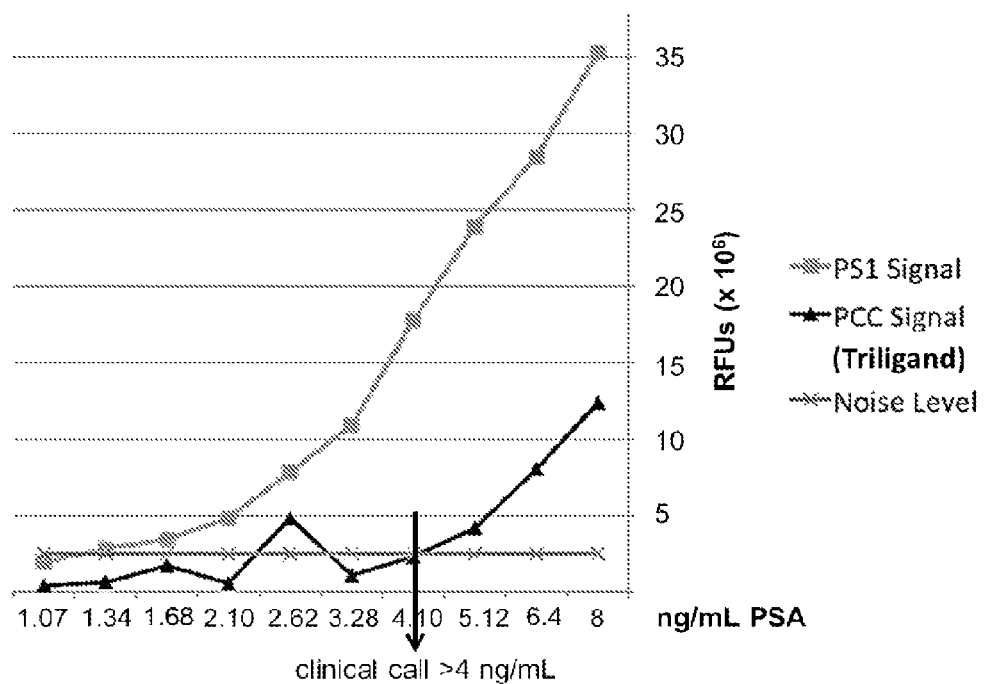
FIG. 14: Sandwich ELISA results of PSA capture agent triligand Tz5Tz5-rrivk, and commercial monoclonal antibody anti-human PSA (PS1 mAb) according to an embodiment of the disclosure, showing a limit of quantitation in the range of cutoff level of 4 ng/mL free PSA.

The results indicate that the synthetic PSA capture agent may be used as a detection antibody when compared to a commercial antibody using a sandwich ELISA. When paired with the appropriate capture antibody (anti-human PSA (PS6)), the assays have a linear range over 10 to 200 ng/mL (FIG. 13). The PSA capture agent triligand exhibited a limit of quantitation (LOQ) in the range of the cutoff level of 4 ng/mL free PSA similar to the research monoclonal antibody (anti-human PSA (PS1), Abcam) (FIG. 14). LOQ, or the lowest statistically reliable quantitative measurement, is dependent on sensitivity, precision (variability), and the noise level of the assay system (~2.5 ng/mL). The interassay variabilities (% CV) for the PSA capture agent triligand and biligand assays are comparative to the research monoclonal antibody down to the level of 3 ng/mL free PSA. The PSA capture agent triligand provides an enhanced sensitivity (>2-fold) over the PSA capture agent biligand; this is predicted from the highly specific in situ click selection process in which the protein target is the catalyst. The analytical performance characteristics of this PSA capture agent ELISA suggested that the synthetic PSA capture agent provided clinically useful detection of PSA from human serum.

Example 4

Comparison of Synthetic PSA Capture Agent to a Commercial PSA Antibody (Dot Blot)

Materials and Methods.

Serially diluted free PSA (Scripps Laboratories #P0725) in PBS pH 7.4 was applied to nitrocellulose by micropipette. The membrane was blocked at 4° C. for 2 hours in 5% non-fat dry milk in TBS (25 mM Tris, 150 mM NaCl, pH 7.25). The membrane was washed with TBS (3×). The biotinylated PSA capture agent was prepared at 0.1 µM in 0.5% milk in TBS+ 0.03% DMSO (v/v) and incubated over the membrane at 4° C. overnight. After washing with TBS (3×), the membrane was further subjected to 0.1 µg/mL HRP-conjugated Streptavidin (Abcam) in TBS containing 0.02% Tween20 (v/v) for 30 min at 4° C. After washing with TBS containing 0.02% Tween20 (v/v) (5×), followed by TBS (2×), the membrane was developed with SuperSignal West Pico Chemiluminescent Enhancer and Substrate Solutions (Pierce, Ill.) and then immediately exposed to HyBlot CL AR film.

Results and Discussion.

Figure 15:
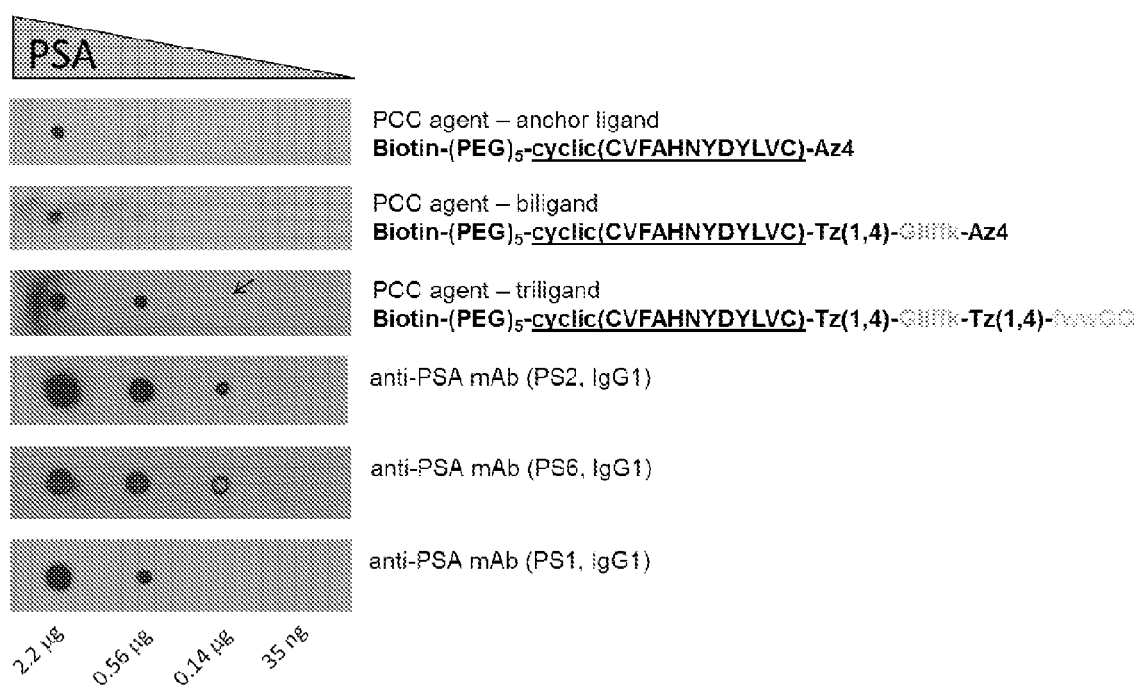
FIG. 15: Dot blot assay of PSA capture agents (anchor ligand, biligand, and triligand) and commercial PSA antibodies (anti-PSA mAb, PS1, PS2 and PS6, IgG1.

PSA capture agents were detected in the range of 2.2 µg to 0.14 µg free PSA. PSA capture agents showed increased affinity from anchor to biligand to triligand, with a lower limit of detection of 0.14 µg free PSA for the PSA capture agent triligand (FIG. 15). The PSA capture agent triligand showed superior performance to anti-human PSA monoclonal antibodies (PS1) and was less sensitive to the commercial PSA monoclonal antibodies (PS2, PS6). The difference in intensity between the PSA capture agent and monoclonal antibody assays may be attributed to a difference in biotinylation (1 biotin/capture agent vs. 10 biotins/monoclonal, on average).

Figure 21:
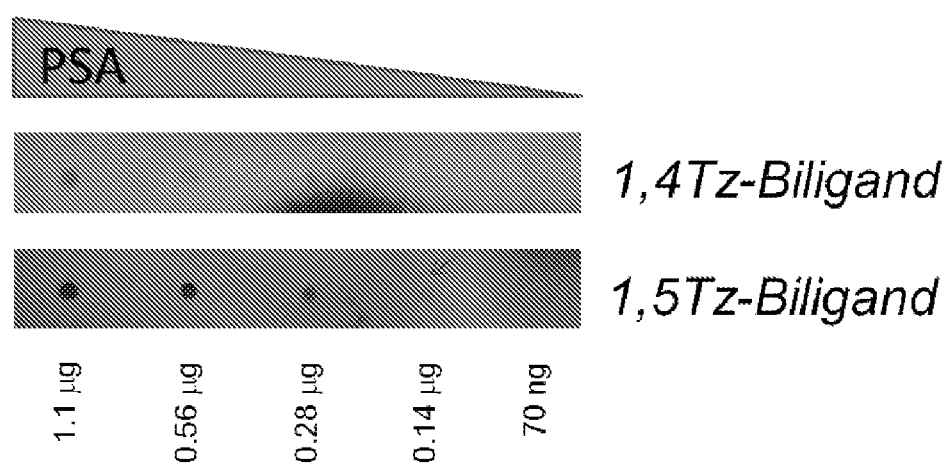
FIG. 21: Dot blot assay of regioisomers of PSA capture agents. PSA capture agents 1,4Tz-biligand and 1,5Tz-biligand differ by only the triazole regioisomer. PSA capture agent 1,5Tz-biligand offers a lower limit of detection than the 1,4Tz-biligand (0.14 μg PSA and 0.28 μg PSA, respectively).

Regioisomers of PSA capture agents (PSA capture agent 1,4Tz-biligand and PSA capture agent 1,5Tz-biligand) showed that the PSA capture agent 1,5Tz-biligand had an improved limit of detection compared to PSA capture agent 1,4Tz-biligand (FIG. 21).

Example 5

Pull-Down Assay and Western Blot

Summary.

The pull-down assay assessed the specificity of a PSA capture agent by measuring its ability to purify a protein from complex media; bound to the protein in buffer or human serum in solution. The PSA/capture agent complex was then physically isolated from the sample with solid-phase affinity resins. The captured samples were separated by SDS-PAGE for Western blot analysis.

Materials and Methods.

Pull-down detection of PSA was performed using a modified immunoprecipitation technique that incorporated PSA capture agent rather than antibody. First, biotinylated PSA capture agent (0.3-0.5 µg/mL) was incubated with 2 mL of 25% human AB male serum (#HS-20, Omega Scientific, Tarzana, Calif.) in TBS at 4° C. overnight. Separately, biotinylated PSA capture agent (0.3-0.5 µg/mL) was incubated at 4° C. overnight with 2 mL of 25% human AB male serum (#HS-20, Omega Scientific, Tarzana, Calif.) in TBS containing 1 µg free PSA. A third sample contained biotinylated PSA capture agent (0.3-0.5 µg/mL) and 1 µg free PSA in 2 mL TBS, and similarly interacted at 4° C. overnight.

Proteins were captured by BSA-blocked Dynabeads® M-280 Streptavidin (Invitrogen, #112-05D) under rotation at 4° C. for 4 hours (50 µL of 50% slurry per pull-down condition). Proteins were eluted from beads in reducing Laemmli buffer, and beads were separated from the serum or buffer by DynaMag™-Spin magnet (Invitrogen, #123-20D). Samples were subjected to 4-20% SDS-PAGE separation and electrophoretically transferred to a nitrocellulose membrane in 25 mM Tris, 192 mM Glycine, pH 8.3, containing 20% (v/v) methanol (Bio-Rad Laboratories, Hercules, Calif.) at 100 V for 45 min. Following transfer, the nitrocellulose membrane was blocked at 4° C. for 2 hours in 5% non-fat dry milk in TBS. The membrane was then washed with TBS (3×), and 0.4 µg/mL Biotinylated goat anti-human Kallikrein 3/PSA antibody (R&D Systems, Minn.) in 0.5% non-fat dry milk in TBS was incubated at 4° C. overnight. After washing with TBS containing 0.02% Tween20 (v/v) (5×), 0.2 µg/mL HRP-conjugated donkey polyclonal secondary antibody to goat IgG (H+L) (Abcam) in 0.5% non-fat dry milk in TBS was added to the membrane (4° C., 1 h incubation). After washing with TBS containing 0.02% Tween20 (v/v) (5×), followed by TBS (2×), the membrane was developed with SuperSignal West Pico Chemiluminescent Enhancer and Substrate Solutions (Pierce, Ill.) and then immediately exposed to HyBlot CL AR film.

Separately, a duplicate 4-20% gel was visualized for total protein content by silver stain (Bio-Rad Laboratories, Hercules, Calif.) to estimate specificity of PSA capture agents in comparison to the Western result.

Results and Discussion.

Figure 16:
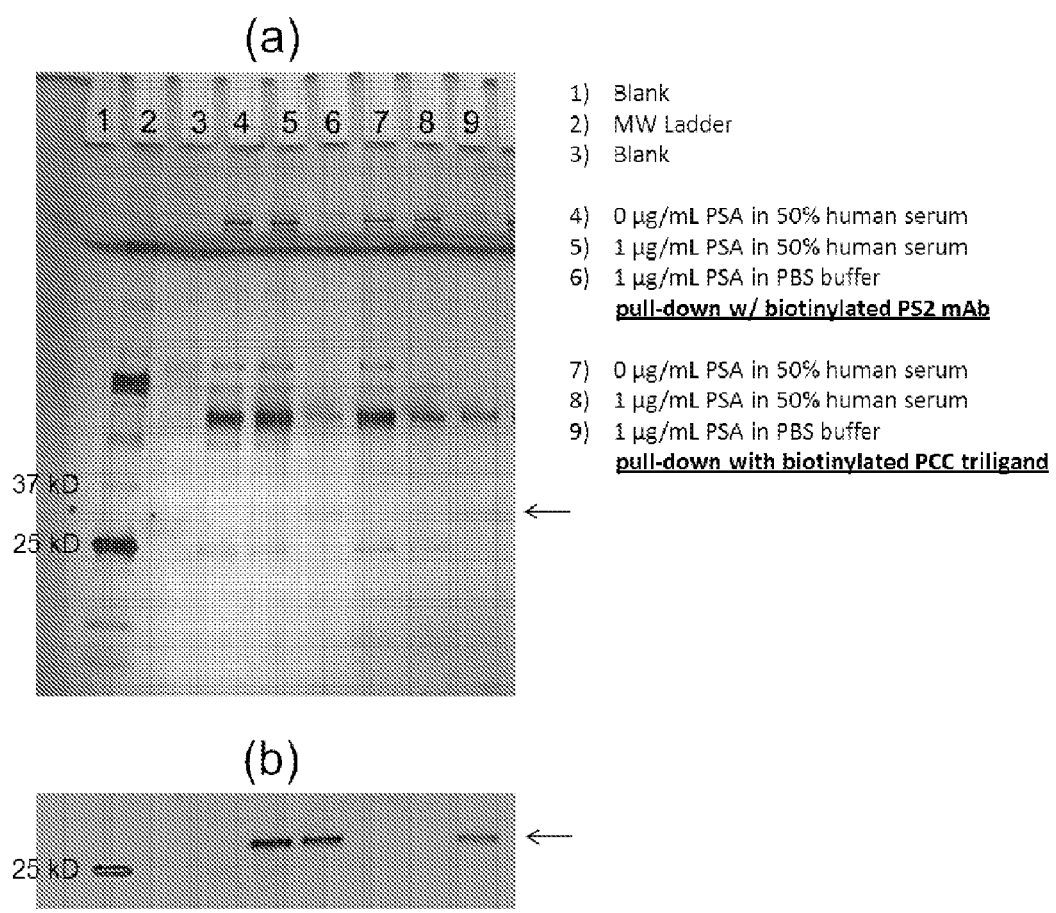
FIG. 16: Pull-down assay of biotinylated PSA capture agent triligand and biotinylated commercial PSA antibodies (PS2 mAb) according to an embodiment of the disclosure: a) SDS-PAGE visualizing results of pull-down assay, silver stained gel; and (b) Western blot for PSA.

PSA capture agent triligand detected free PSA in buffer (FIG. 16). Additional modifications to the PSA capture agent sequence/structure are expected to contribute to highly specific pull-down from human serum.

Example 6

Serum Stability

Summary.

Proteolytic stability is an important factor for the use of peptides in in vivo applications and for serum protein diagnostics. Most natural peptides have to be modified to prevent enzymatic degradation. Several approaches including the use of D-amino acids, non-natural amino acids, and cyclization have been used to improve capture agent stability.

Materials and Methods.

Stability was studied by mixing 200 µg capture agent in TBS containing 25% (v/v) human AB male serum (HS-20, Omega Scientific, Tarzana, Calif.) in 800 µL total volume (see, e.g., Pakkala 2007). Peptides were incubated at 37° C., and 100 µL aliquots were taken at time=0 min, after 30 min, and then after every hour up to 4 h. A final aliquot was taken after 24 h. The peptide was separated from plasma proteins on a Microcon centrifugal filter device (Microcon YM-10, MWCO=10 kDa, Millipore, Bedford, Mass.) by centrifugation at 12,000 rpm using a Beckman Coulter refrigerated microcentrifuge (Brea, Calif.) for 20 min. The filtrates were examined by analytical HPLC (C18 column, linear gradient of 0→50% B over 30 min, where A=$H_2O$+0.1% TFA and B=ACN+0.1% TFA), followed by Bruker UltrafleXtreme MALDI mass spectrometry.

Two control assays were performed in parallel and subjected to the same conditions as above: 1) capture agent in TBS, and 2) TBS containing 25% (v/v) human AB male serum.

Results and Discussion.

Figure 17:
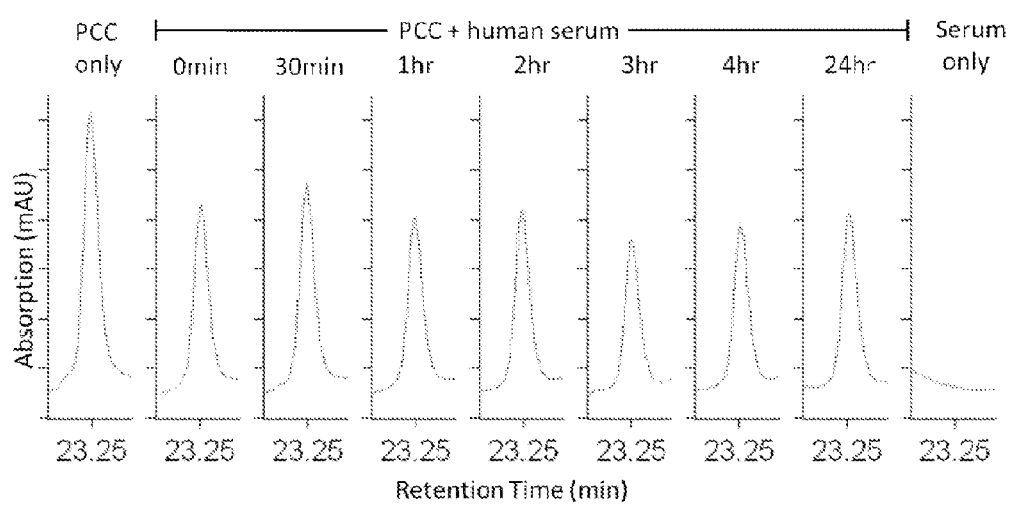
FIG. 17: Serum stability assay of PSA capture agent triligand, shown by HPLC analysis of PSA capture agent triligand incubated with human serum.

After a 4-hour incubation with human serum at 37° C., the PSA capture agent triligand was still intact. After 24 hours no fragmentation was observed by HPLC analysis (FIG. 17). The data suggest that the PSA capture agent triligand is stable to proteolytic degradation in human serum for more than 24 h at physiological temperature and buffer. Our results indicate that cyclization is an efficient and simple approach to improve resistance to proteolytic digestion for sequence segments containing (natural) L-amino acids, and that D-amino acids and non-natural amino acids are intrinsically stable elements. This approach, without any sequence modifications, could be useful for designing peptides for in vivo studies.

Example 7

Long-Term Stability of Synthetic PSA Capture Agents

Figure 18:
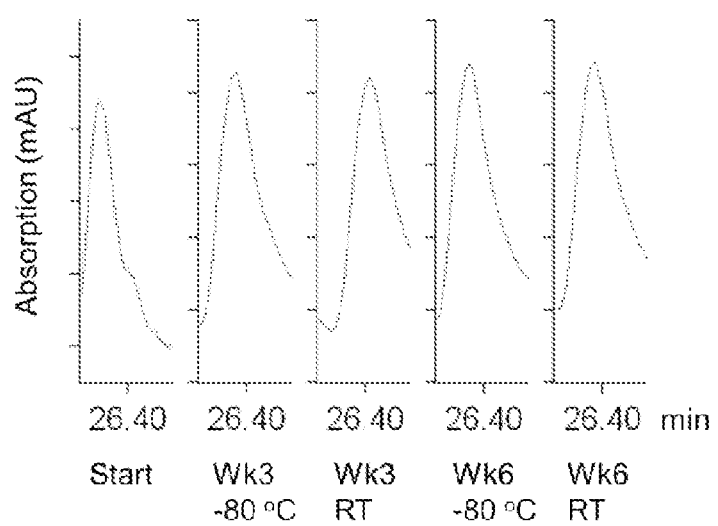
FIG. 18: Long term stability assay of PSA capture agent triligand, shown by HPLC analysis of PSA capture agent triligand stored as a lyophilized powder at room temperature (RT) or at a temperature of −80° C. for 3 weeks and 6 weeks respectively.

Long-term stability of the synthetic PSA capture agents was assessed by storing the capture agents as lyophilized powders in air at room temperature and –80° C. for three months. Fractions were taken periodically and examined by analytical HPLC (C18 column, linear gradient of 0→50% B over 30 min, where A=$H_2O$+0.1% TFA and B=ACN+0.1% TFA), followed by Bruker UltrafleXtreme MALDI mass spectrometry. HPLC analysis showed that the capture agent triligand is stable for more than 6 weeks as a lyophilized powder regardless of storage temperature (FIG. 18).

Example 8

Activity Assay

Materials and Methods.

The enzyme activity of free PSA was studied in the presence of capture agent and the chymotrypsin substrate Suc-Arg-Pro-Tyr-pNA (AnaSpec, San Jose, Calif.) (see, e.g., Wu 2000). PSA (333 nM) was incubated with a 1-100-fold fold molar excess of capture agent in TBS (25 mM Tris, 150 mM NaCl) buffer, pH 7.8, for 1 hour at 23° C. Separately, the inhibitory effect of $Zn^{2+}$ on the enzyme activity of PSA was studied by including 1-200 μM $ZnCl_2$ in the reaction buffer as a control. After addition of substrate to a final concentration 0.4 mM, the absorbance was monitored at 5-min intervals over 80 min at 405 nm on a Beckman Coulter DTX880 photometer (Brea, Calif.). Enzyme activity of PSA was tested in the absence of both $Zn^{2+}$ and capture agent to provide a measure of basal activity. All assays were performed in triplicate.

Results and Discussion.

Figure 19:
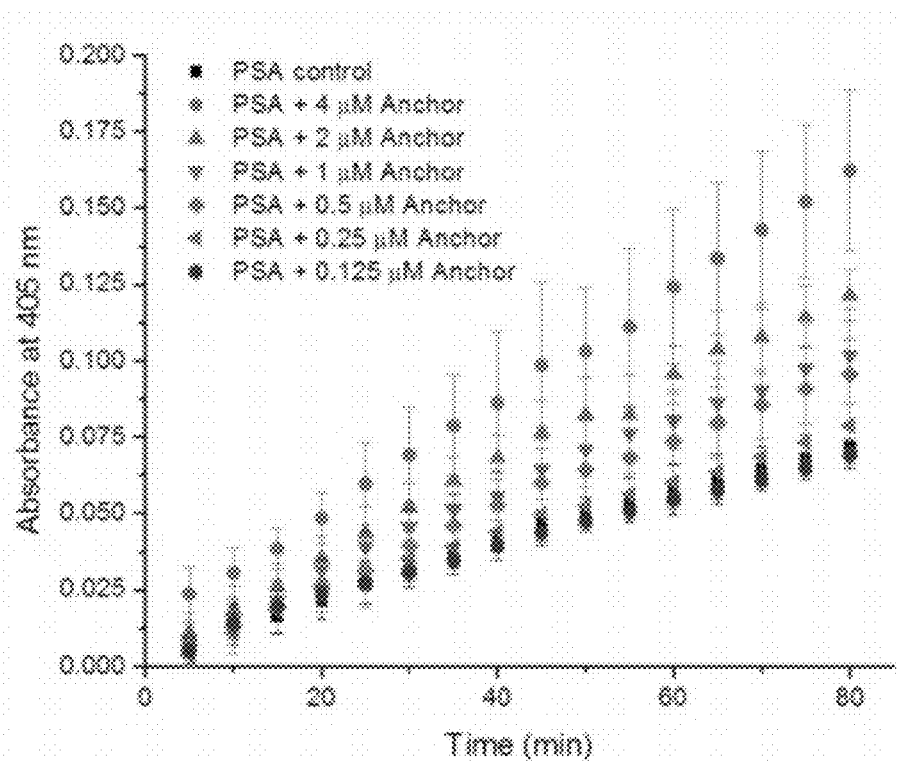
FIG. 19: Enzyme activity assay of PSA enhanced by PSA capture agents: a) PSA anchor ligand; b) PSA capture agent biligand; and c) negative control zinc chloride.
Figure 19:
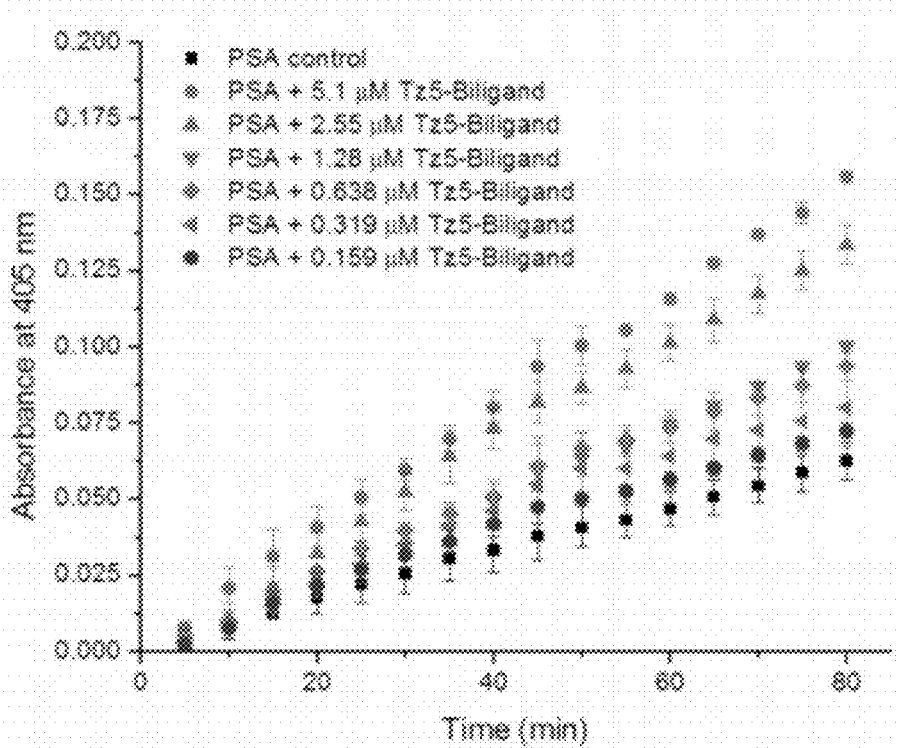
Figure 19:
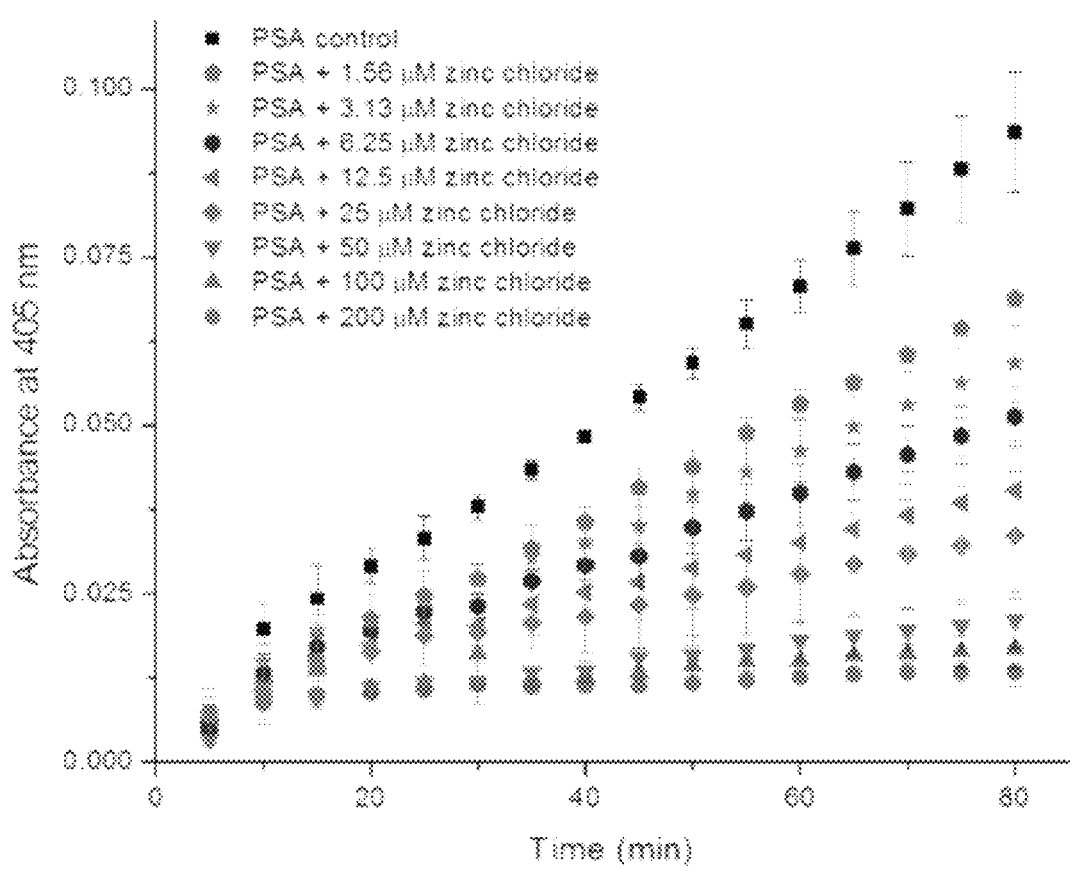
Figure 20:
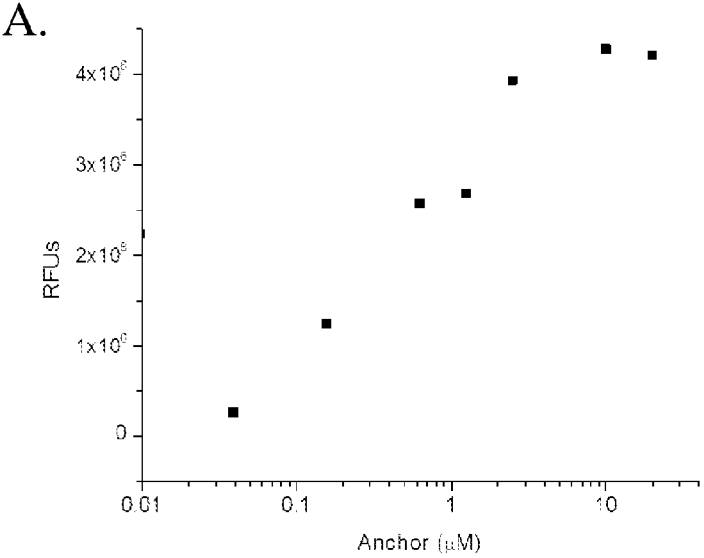
FIG. 20: Scatchard plot of biotinylated PSA capture agent: A) PSA capture agent ligand; and B) determination of dissociation constant (KO.
Figure 20:
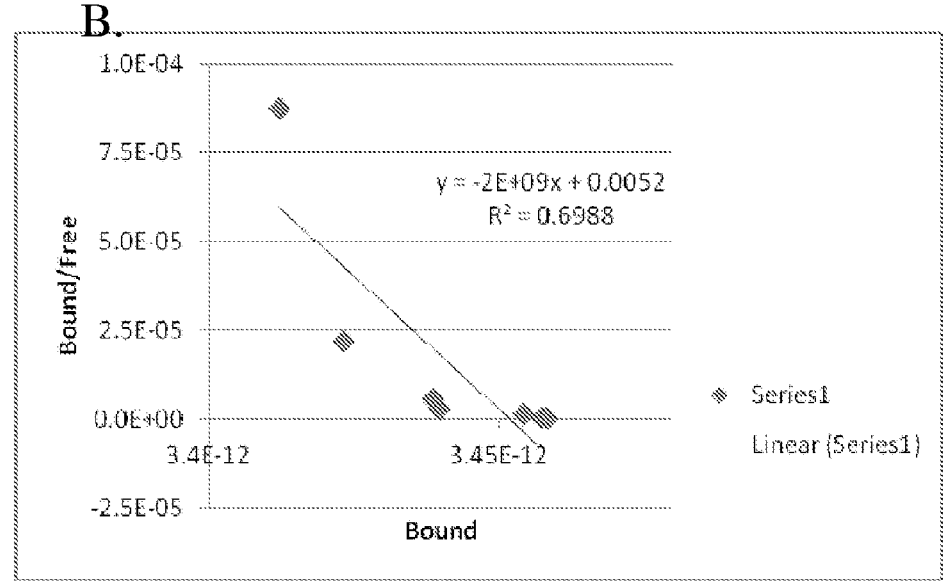

The enzyme activity of PSA was enhanced by PSA capture agent, stimulating PSA activity against the chromogenic substrate at approximately three-fold. The effect was dependent on concentration of the capture agent, and half maximal stimulation was detected with concentration in the micromolar range. The minimum peptide concentration affecting the activity varied between 0.250 μM for the Anchor Ligand (FIG. 19A) and 0.159 μM for the capture agent biligand (FIG. 19B). It has been suggested that the Anchor Ligand binds in the vicinity of the active site and possibly changes the conformation of the active site to make the catalytic pocket more accessible to the synthetic substrate (Wu 2000). If the capture agents identified in this invention also increase the activity of PSA against natural substrates, they would be potentially useful for studying the biological role of PSA in prostate pathology and physiology. Interestingly, none of these peptides inhibited enzyme activity. $Zn^{2+}$ inhibits the enzyme activity of PSA and, for comparison, contributes the behavior shown in FIG. 19C.

Example 9

Scatchard Plots

Summary.

Scatchard analysis was performed to determine the equilibrium dissociation constant ($K_D$) for the capture agent.

Materials and Methods.

MAXISORP™ microtiter plates were coated with 2 μg/mL free PSA (Scripps Laboratories #P0725) in PBS pH 7.4 over 2 h at room temperature. After washing each well with PBS (3×), the plate was filled with 5% non-fat dry milk in TBS (25 mM Tris, 150 mM NaCl, pH 7.25) and blocked for 2 h at room temperature. The plate was washed with 1% BSA in TBS (5×), and then serially diluted biotinylated capture agent in 1% BSA in TBS+0.1% DMSO (v/v) was incubated for 2 h at room temperature. After washing all microwells with 1% BSA in TBS (5×), 0.1 μg/mL Streptavidin Poly-HRP conjugate (Pierce, Ill.) in 1% BSA in TBS was incubated for 30 min at room temperature. The plate was aspirated and washed with 1% BSA in TBS (10×), followed by TBS (2×), and then developed by adding QuantaRed™ Enhanced Chemifluorescent HRP Substrate (Pierce, Ill.). Using an excitation wavelength of 535 nm, fluorescent emission at 595 nm was recorded by Beckman Coulter DTX880 photometer (Brea, Calif.) as a function of capture agent concentration. Assays were performed in triplicate.

Saturation binding data were visualized by the Scatchard method for determination of $K_D$. Bound biotinylated capture agent was estimated from a titration series of Streptavidin Poly-HRP conjugate, assuming 1:1 biotin:streptavidin.

Example 10

MicroPET/CT Imaging and Biodistribution Analysis

DOTA-labeled 1,5Tz-biligand will be labeled with $^{64}Cu$ and administered to mice via a 100 μg I.V. tail vein injection. Whole-body imaging will be carried out with microPET scanners using a two hour dynamic scan, followed by microCT imaging. 10 minute static microPET scans will also be carried out at 4 and 6 hours. Biodistribution of labeled capture agent among various organs (e.g., bladder, kidney, gall bladder, liver, brain, and blood) will be analyzed to evaluate clearance and accumulation.

Example 11

MRM Assay

Multiple Reaction Monitoring (MRM) is a mass spectrometry-based assay that enables highly multiplexed assays to be developed rapidly. Depending on assay parameters and mass spectrometric device, up to 100 protein assays can be multiplexed into a single MRM sample analysis. Hundreds of protein assays can be performed on a single blood sample via aliquoting the sample.

MRM assays for PSA will be developed. PSA capture agents are immobilized on 100 nanoliter nanoaffinity columns are used to enrich specific PSA peptides along with spiked stable-isotope-labeled internal standards of the same sequence. Upon elution from the anti-peptide PSA capture agent supports, electrospray mass spectrometry is used to quantitate the peptides (natural and labeled).

Typically, two peptides and two transitions per peptide will be monitored for each protein giving four data points per assay. Synthetic peptides will be utilized to develop the MRM assays thereby determining peptide retention time and transition masses. Due to the number of proteins (over 100) the protein assays will be grouped into two or three batches for separated MRM runs.

In addition to PSA included in the MRM assays, other cancers or prostate diseases may be included in the MRM assays as part of a protein panel. These markers will be obtained from the literature or from proprietary databases.

Sample Runs.

Each sample will be divided into 2 or 3 aliquots for MRM runs. Samples will be spiked with peptide standards for normalization of quantification across sample runs. Samples from each cohort will be matched based on clinical data (gender, age, collection site, etc.) and matched samples will be run sequentially through the MRM assays to minimize analytical bias. Protein assay measurements will be obtained for each protein in each sample.

Evaluation.

For each protein, a statistical test (such as a false discovery rate adjusted one-side paired t-test) will be used to determine if the protein distinguishes cancerous samples above a certain spot size (say, e.g., 10 mm) from non-cancerous samples. Pairing of samples in the statistical test will be determined by the matching of samples as described above. As there are four data points per protein, at least three of the four data points must exhibit a significant statistical difference.

To verify that a specific panel of proteins is, collectively, a diagnostic panel that distinguishes cancerous samples above a certain spot size (e.g., 10 mm) from non-cancerous samples, the following analysis is performed. All data points for the proteins on the panel are treated as if data points from a single protein and submitted to the paired statistical test. If the false discovery rate adjusted p-value of this test is significant (e.g., below 5%) then the panel is verified as diagnostic. The false discovery rate can be estimated using many methods including permutation testing where the samples from all cohorts are iteratively randomized to provide an estimate of the false discovery rate.

As stated above, the foregoing are merely intended to illustrate the various embodiments of the present invention. As such, the specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference as if fully set forth herein.

REFERENCES

1. Acevedo et al., Clin Chem Acta 317:55-63 (2002)
1. Agnew et al., Angew Chem Int Ed 48:4944-4948 (2009)
2. Boren et al., J Am Chem Soc 130:8923-8930 (2008)
3. Fields & Noble, Int J Pept Protein Res 35:161-214 (1990)
4. Jeong & Lee, J Microbiol Biotechnol 17:840-846 (2007)
5. Lee et al., J Comb Chem 10:807 (2008)
6. Lee et al., Anal Chem 82:672-679 (2010)
7. Pakkala et al., J Pept Sci 13:348-353 (2007)
8. Wu et al., Eur J Biochem 267:6212-6220 (2000)

What is claimed is:

1. A synthetic detection agent comprising a multi-ligand prostate specific antigen (PSA)-targeted capture agent that specifically binds PSA in serum, wherein the capture agent is a triligand; wherein the triligand comprises an anchor ligand, a secondary ligand, and a tertiary ligand; wherein the linkage between one or more of the anchor ligand, secondary ligand, and tertiary ligand comprises a 1,5-substituted-1,2,3-triazole residue (Tz5) or a 1,4-substituted-1,2,3-triazole residue (Tz4):

Tz4

Tz5

2. The detection agent of claim 1, wherein the anchor ligand comprises a polypeptide comprising an amino acid sequence of SEQ ID NO:1 and wherein the secondary ligand comprises a polypeptide comprising an amino acid sequence of SEQ ID NO:2.

3. The detection agent of claim 1, wherein the tertiary ligand comprises a polypeptide comprising an amino acid sequence selected from the group consisting of SEQ ID NO:3 and 4.

4. The detection agent of claim 2, wherein the tertiary ligand comprises a polypeptide comprising an amino acid sequence of SEQ ID NO:3.

5. The detection agent of claim 2, wherein the tertiary ligand comprises a polypeptide comprising an amino acid sequence of SEQ ID NO:4.

6. The detection agent of claim 1, wherein the capture agent is a cyclic triligand resistant to proteolytic digestion.

7. The detection agent of claim 1, wherein the capture agent is stable in storage as a lyophilized powder.

8. The detection agent of claim 1, wherein the capture agent is stable in storage at temperature of about −80° C. to about 40° C.

9. The detection agent of claim 1, wherein the capture agent is stable in storage at room temperature.

10. The detection agent of claim 1, wherein the capture agent is stable in human serum for at least 24 hours.

11. The detection agent of claim 1, wherein the capture agent is stable at a pH in the range of (3.0-8.0).

12. The detection agent of claim 1, wherein the capture agent is labeled with copper-DOTA.

13. The detection agent of claim 1, wherein the capture agent is labeled with biotin.

14. The detection agent of claim 1, wherein the capture agent binds to a non-canonical epitope on a protein.

15. The detection agent of claim 1, wherein the capture agent is an immunotherapeutic.

16. The detection agent of claim 1, wherein the capture agent is a diagnostic agent.

17. The detection agent according to claim 1, wherein the anchor ligand is a cyclic L-peptide, the secondary ligand is a D-peptide, and the tertiary ligand is a D-peptide.

18. The detection agent according to claim 1, wherein the linkages between the anchor ligand and the secondary ligand and between the secondary ligand and the tertiary ligand comprise Tz5.

19. The detection agent according to claim 1, comprising a structure selected from the group consisting of Tz-4-triligand and Tz5-triligand:

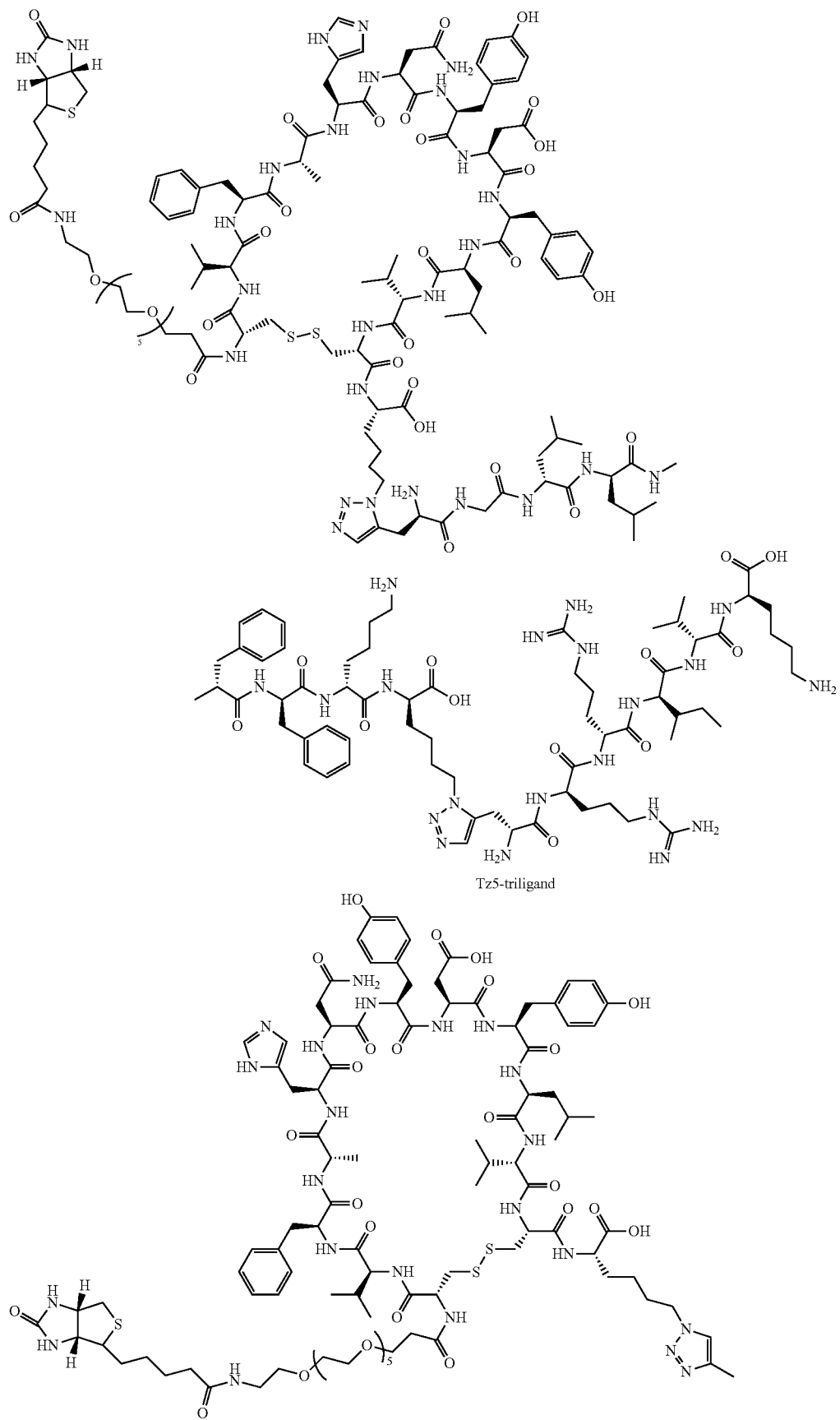

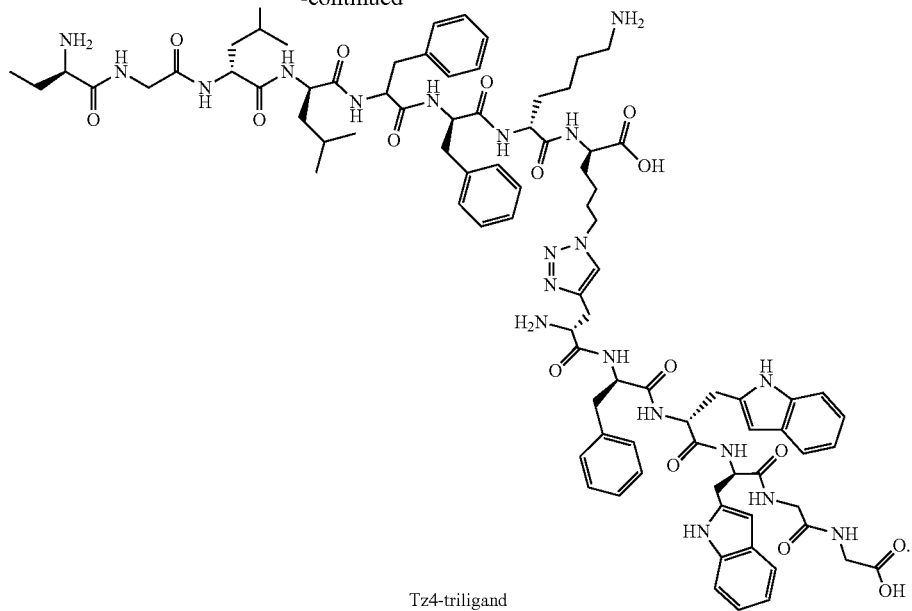

Tz4-triligand

20. A method of preparing the Tz5-triligand according to claim 19 comprising:
   a) synthesizing side-chain-protected biotin-PEG$_5$-CV-FAHNYDYLVC (SEQ ID NO:1), side-chain-protected biotin-PEG$_5$ anchor synthetic block (I), side-chain-protected Tz5-Gllffk (SEQ ID NO:2), side-chain-protected secondary synthetic block (I), and side-chain-protected Tz5-rrivk (SEQ ID NO:3), side-chain-protected tertiary synthetic block (I), having the following structures:

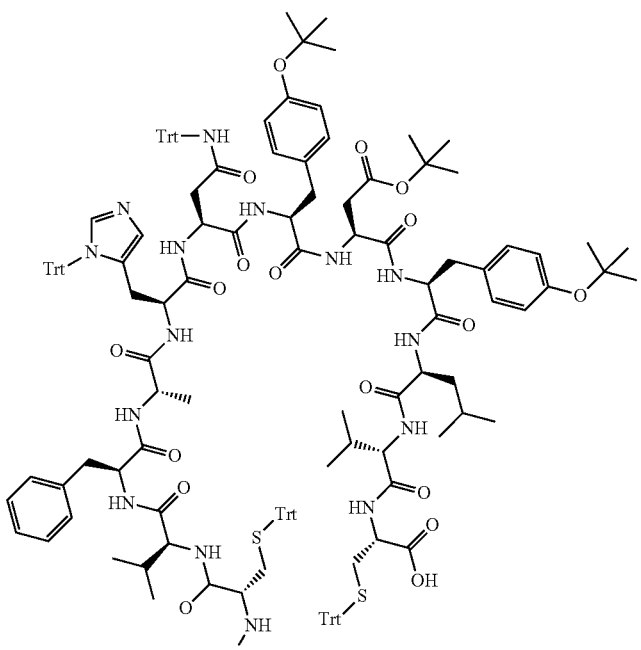

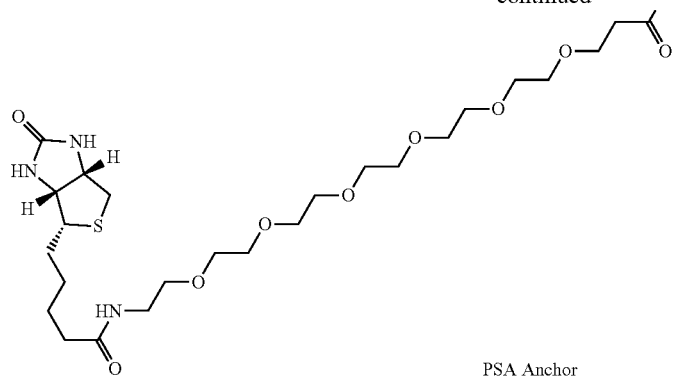
PSA Anchor
Chemical Formula: $C_{149}H_{202}N_{18}O_{27}S_3$
Molecular Weight: 2773.4976
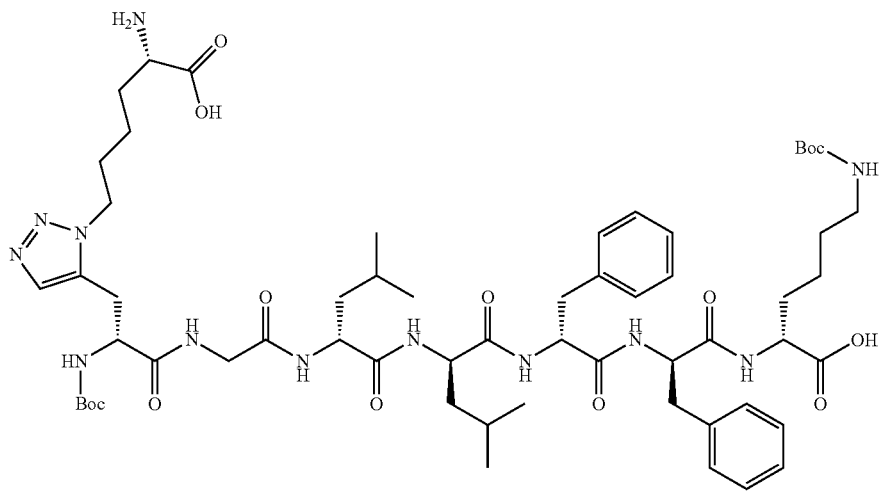
Secondary
Chemical Formula: $C_{59}H_{90}N_{12}O_{14}$
Molecular Weight: 1191.4179
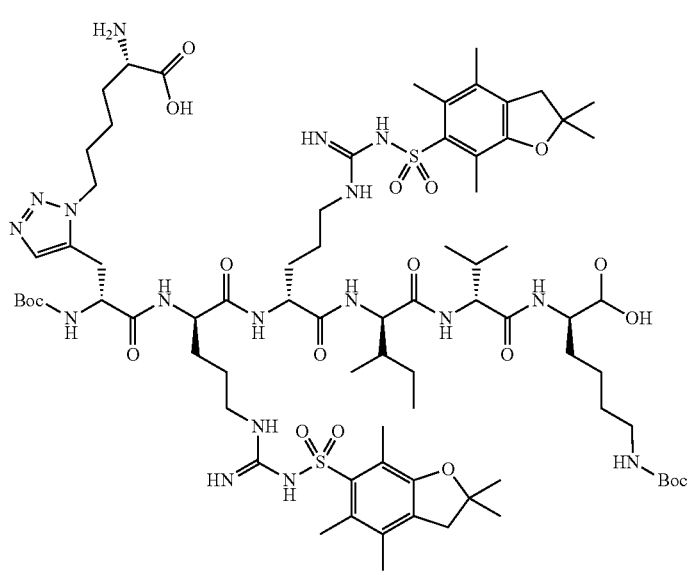
Tertiary
Chemical Formula: $C_{75}H_{123}N_{17}O_{19}S_2$
Molecular Weight: 1643.0223 b) coupling the side-chain-protected biotin-PEG$_5$ anchor synthetic block (I) and the side-chain-protected secondary synthetic block (I) to form a side-chain protected biotin-PEG$_5$-CVFAHNYDYLVC(SEQ ID NO:1)-Tz5-Gllffk (SEQ ID NO:2), side-chain-protected biotin PEG$_5$-PSA Tz5-biligand synthetic block (I), having the following structure:

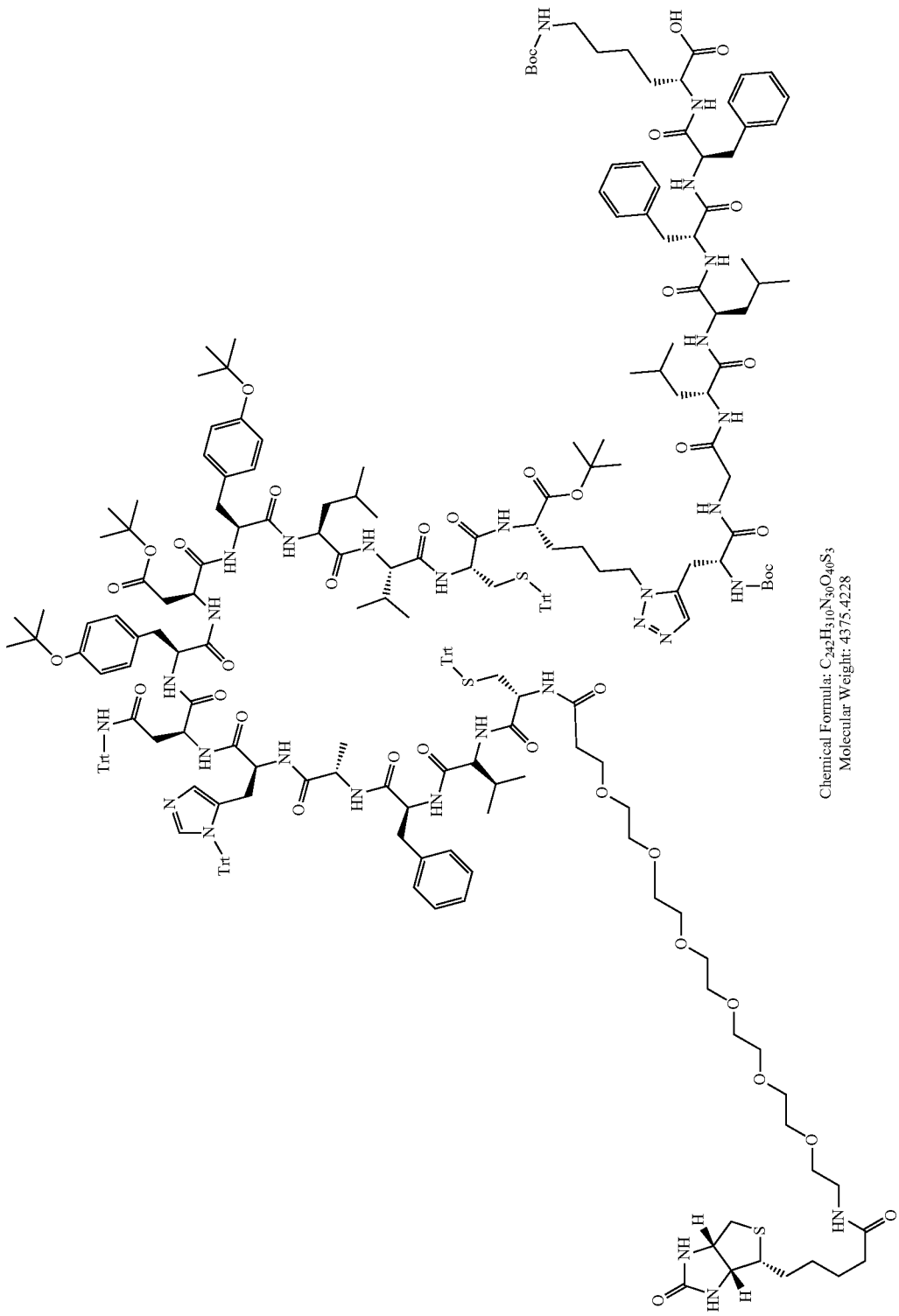

c) coupling side-chain-protected biotin-PEG$_5$-Tz5-biligand synthetic block (I) with the side-chain-protected tertiary synthetic block (I) to form side-chain-protected biotin-PEG$_5$-CVFAHNYDYLVC(SEQ ID NO:1)-Tz5-Gllffk(SEQ ID NO:2)-Tz5-rrivk (SEQ ID NO:3), side-chain protected Biotin-PEG$_5$-PSA Tz5-triligand synthetic block (I), having the following structure:

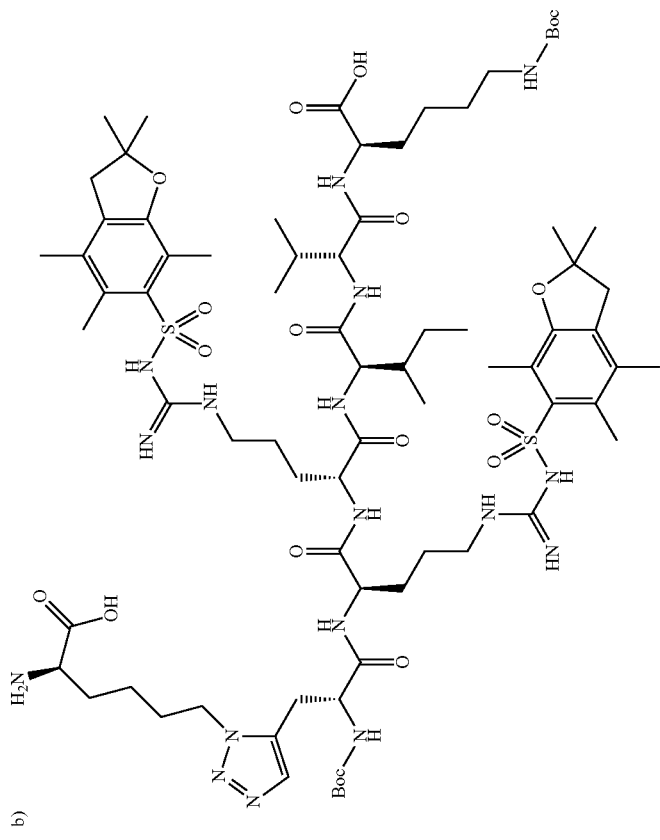

-continued
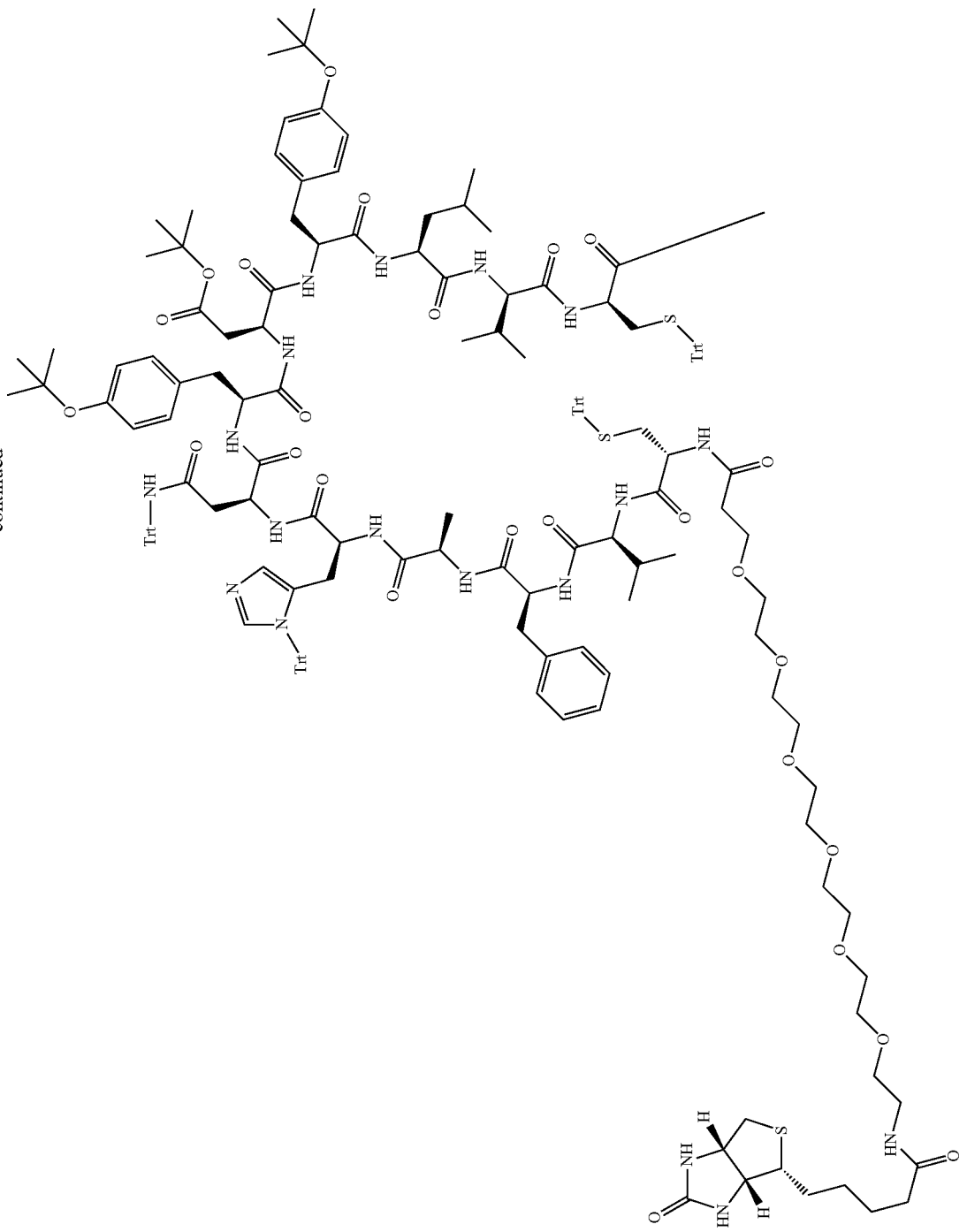

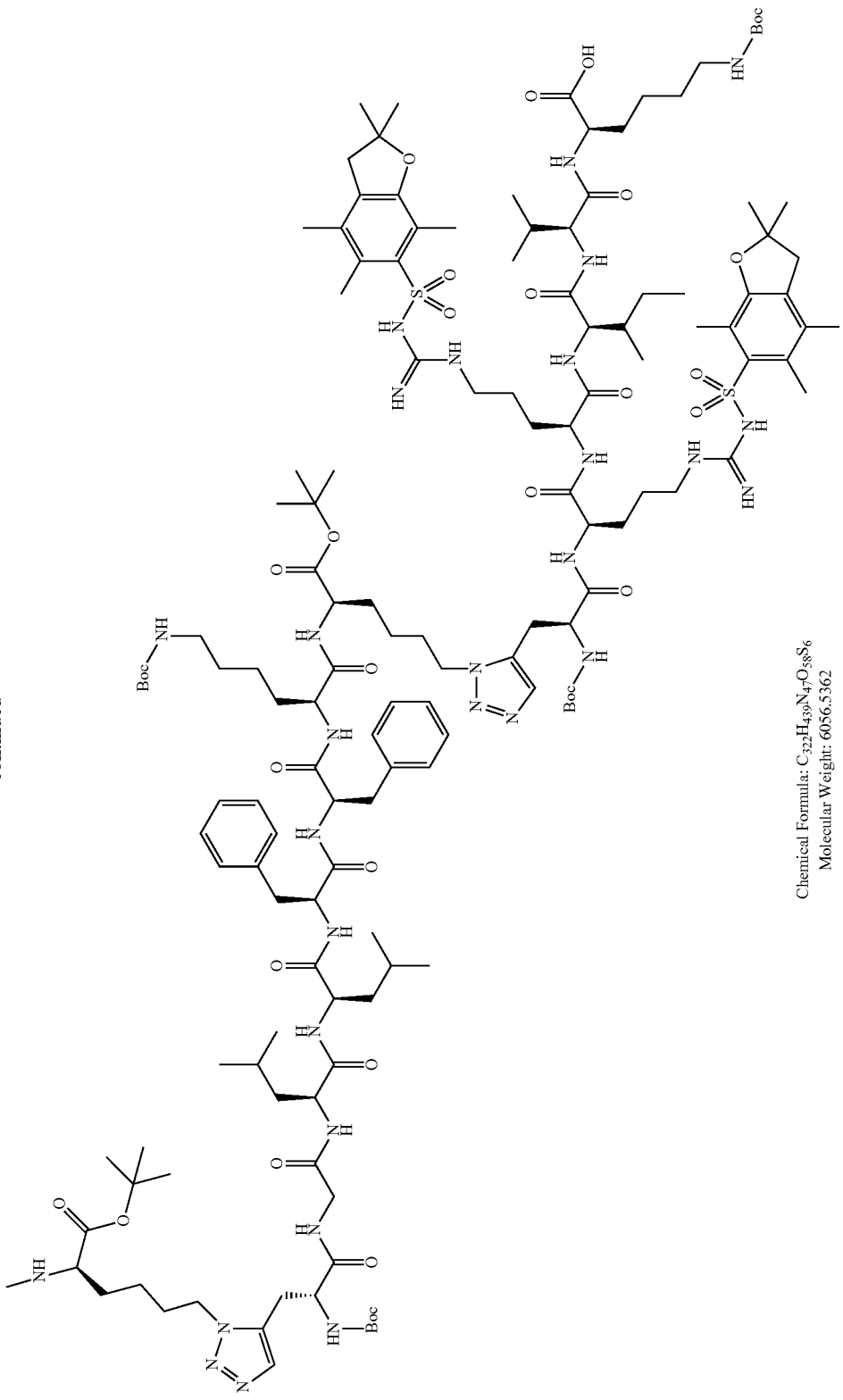

d) deprotecting the side-chain-protected Biotin-PEG$_5$-PSA Tz5-triligand synthetic block (I) to form biotin-PEG$_5$-CVFAHNYDYLVC(SEQ ID NO:1)-Tz5-Gllffk(SEQ ID NO:2)-Tz5-rrivk(SEQ ID NO:3); and
e) forming disulfide bond to provide biotin-PEG$_5$-cyclic (CVFAHNYDYLVC(SEQ ID NO:1))-Tz5-Gllffk(SEQ ID NO:2)-Tz5-rrivk (SEQ ID NO:3), biotin-PEG$_5$-PSA Tz5-triligand (I), having the following structure:
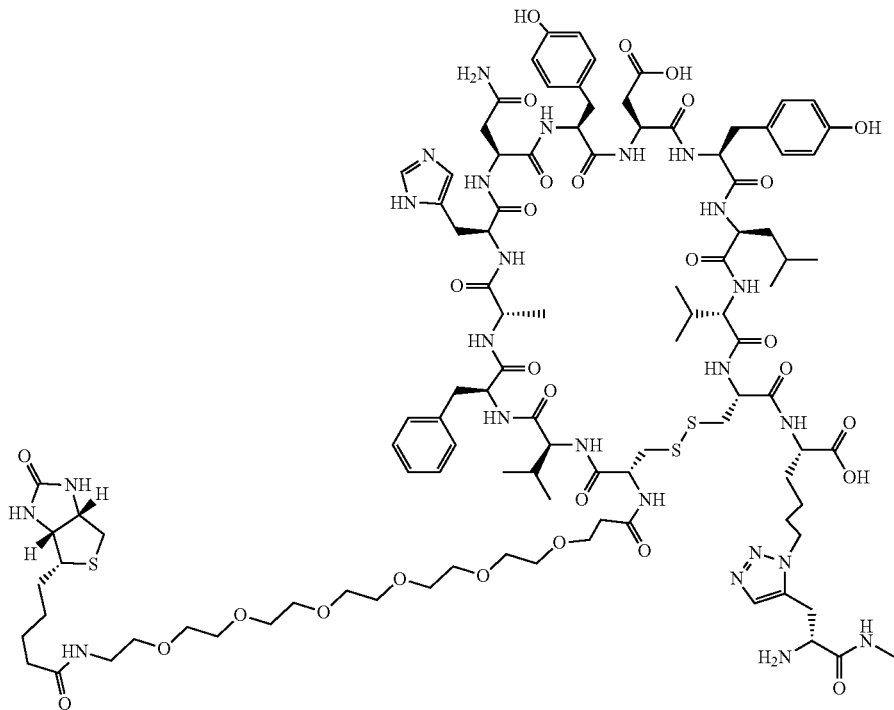
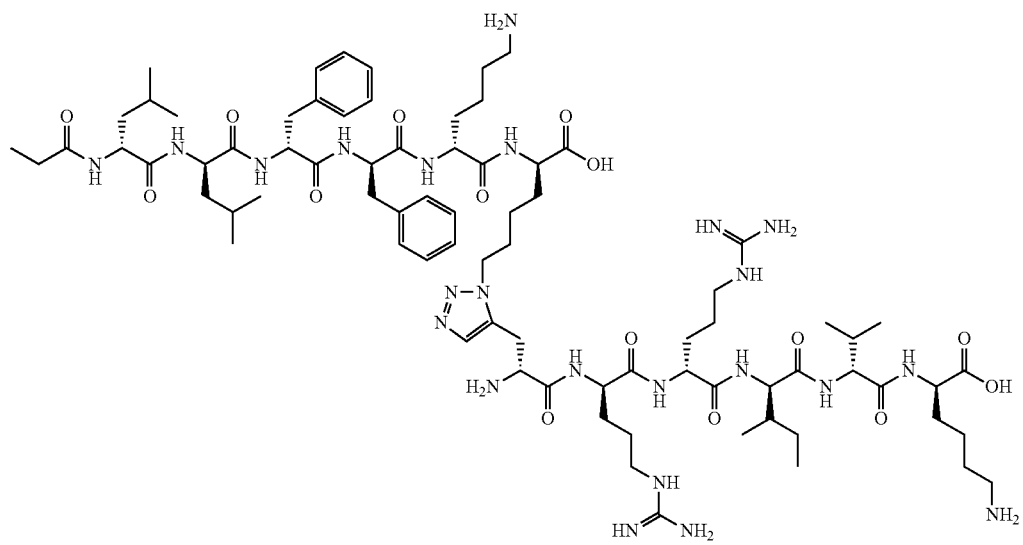

-continued

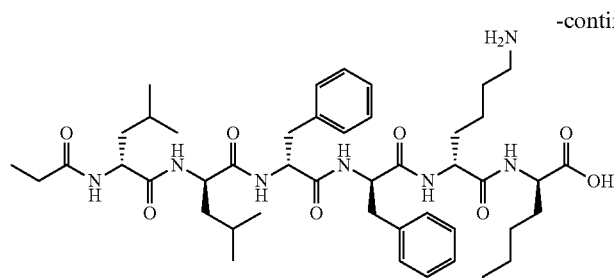
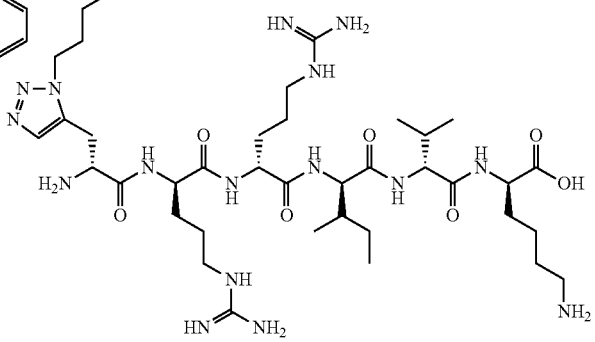

wherein PEG$_5$ is —(NH—(C$_2$H$_4$—O—)$_5$—C(O))—, Trt is trityl, Boc is tert-butyloxycarbonyl), and TFA is trifluoroacetic acid.

21. A method of developing a PSA-targeted capture agent according to claim 1 comprising the following steps:
   a) contacting PSA with biotin-PEG$_5$-cyclic (CVFAHNYDYLVC(SEQ ID NO:1))-Az4 ("azide-modified PSA-PCC anchor selection block (I)") to provide a PSA-anchor complex;
   b) contacting the PSA-anchor complex with a first plurality of candidate peptides to select a PSA-PCC secondary ligand, the peptides coupled with a D-propargylglycine at its N-terminus;
   c) providing a PSA-PCC biligand by forming a 1,2,3-triazole linkage between the PSA-PCC anchor selection block and the PSA-PCC secondary ligand, wherein the azido and alkynyl group of the anchor selection block and the secondary ligand are brought in close proximity by binding to the target protein to provide a bead modified with the PSA-PCC biligand;
   d) selecting the beads modified with the PSA-PCC biligand; removing the PSA-PCC biligands from the beads modified with the PSA-PCC biligand;
   e) sequencing the PSA-PCC secondary ligand of the PSA-PCC biligand;
   f) preparing a biotin-PEG$_5$-cyclic (CVFAHNYDYLVC (SEQ ID NO:1))-PSA secondary ligand-Az4 ("azide-modified PCC biligand selection block (I)"); and repeating steps of a) to f) until a PSA capture agent having desired antibody-like properties is screened; wherein PEG$_5$ is —(NH—(C$_2$H$_4$—O—)$_5$—C(O))— and Az4 is L-azidolysine.

22. A method of detecting PSA using the PSA capture agent of claim 1 in an immunoassay wherein the PSA capture agent replaces an antibody or its equivalent in the immunoassay.

23. The method of claim 22, wherein the immunoassay is selected from the group of Western blot, pull-down assay, dot blot, and ELISA.

* * * * *

SEQUENCE LISTING

```
<160> NUMBER OF SEQ ID NOS: 4

<210> SEQ ID NO 1
<211> LENGTH: 12
<212> TYPE: PRT
<213> ORGANISM: Artificial Sequence
<220> FEATURE:
<223> OTHER INFORMATION: PSA capture agent anchor ligand

<400> SEQUENCE: 1

Cys Val Phe Ala His Asn Tyr Asp Tyr Leu Val Cys
1               5                   10

<210> SEQ ID NO 2
<211> LENGTH: 6
<212> TYPE: PRT
<213> ORGANISM: Artificial Sequence
<220> FEATURE:
<223> OTHER INFORMATION: PSA capture agent secondary ligand

<400> SEQUENCE: 2

Gly Leu Leu Phe Phe Lys
1               5

<210> SEQ ID NO 3
<211> LENGTH: 5
<212> TYPE: PRT
<213> ORGANISM: Artificial Sequence
```

```
<220> FEATURE:
<223> OTHER INFORMATION: PSA capture agent tertiary ligand

<400> SEQUENCE: 3

Arg Arg Ile Val Lys
1               5

<210> SEQ ID NO 4
<211> LENGTH: 5
<212> TYPE: PRT
<213> ORGANISM: Artificial Sequence
<220> FEATURE:
<223> OTHER INFORMATION: PSA capture agent tertiary ligand

<400> SEQUENCE: 4

Phe Trp Trp Gly Gly
1               5
```